United States Patent
Ohishi et al.

(10) Patent No.: US 10,575,811 B2
(45) Date of Patent: Mar. 3, 2020

(54) X-RAY DIAGNOSIS APPARATUS, IMAGE PROCESSING APPARATUS, AND IMAGE DIAGNOSIS AIDING METHOD

(71) Applicants: TOHOKU UNIVERSITY, Sendai-shi (JP); Toshiba Medical Systems Corporation, Otawara-shi (JP)

(72) Inventors: Satoru Ohishi, Otawara (JP); Koichi Chida, Sendai (JP)

(73) Assignees: TOHOKU UNIVERSITY, Sendai-shi (JP); Canon Medical Systems Corporation, Otawara-shi (JP)

( * ) Notice: Subject to any disclaimer, the term of this patent is extended or adjusted under 35 U.S.C. 154(b) by 237 days.

(21) Appl. No.: 15/634,366

(22) Filed: Jun. 27, 2017

(65) Prior Publication Data

US 2017/0367673 A1  Dec. 28, 2017

(30) Foreign Application Priority Data

Jun. 28, 2016  (JP) .................................. 2016-127990

(51) Int. Cl.
*A61B 6/00*  (2006.01)
*A61M 5/00*  (2006.01)

(52) U.S. Cl.
CPC .......... *A61B 6/5217* (2013.01); *A61B 6/4441* (2013.01); *A61B 6/463* (2013.01); *A61B 6/481* (2013.01); *A61B 6/504* (2013.01); *A61B 6/5205* (2013.01); *A61B 6/5294* (2013.01); *A61B 6/547* (2013.01); *A61M 5/007* (2013.01)

(58) Field of Classification Search
USPC ....................................................... 600/431
See application file for complete search history.

(56) References Cited

U.S. PATENT DOCUMENTS

| | | | | |
|---|---|---|---|---|
| 2010/0080354 | A1* | 4/2010 | Fu | A61N 5/1049 378/65 |
| 2014/0205061 | A1* | 7/2014 | Sakaguchi | A61B 6/486 378/41 |

(Continued)

FOREIGN PATENT DOCUMENTS

| | | |
|---|---|---|
| JP | 2004-337538 | 12/2004 |
| JP | 2005-27359 | 1/2005 |

(Continued)

*Primary Examiner* — Nicole F Lavert
(74) *Attorney, Agent, or Firm* — Oblon, McClelland, Maier & Neustadt, L.L.P.

(57) ABSTRACT

An X-ray diagnosis apparatus comprises processing circuitry. The processing circuitry is configured: to generate first subtraction image by using a first image acquisition condition; to generate second subtraction image by using a second image acquisition condition that are substantially same as the first image acquisition condition; to generate first color image by using a first processing condition, each pixel of the first color image having a color according to a temporal transition at a corresponding position of the first subtraction image; to generate, by using a second processing condition that is substantially same as the first processing condition, second color image, each pixel of the second color image having a color according to a temporal transition at a corresponding position of the second subtraction image; and to cause a stereoscopic image to be displayed on the basis of the first color image and the second color image.

19 Claims, 17 Drawing Sheets

(56) References Cited

U.S. PATENT DOCUMENTS

| | | | |
|---|---|---|---|
| 2015/0150526 A1 | 6/2015 | Ohishi | |
| 2015/0150527 A1 | 6/2015 | Ohishi | |
| 2016/0000393 A1* | 1/2016 | Vedantham | A61B 6/025 378/27 |
| 2016/0015348 A1 | 1/2016 | Ohishi | |
| 2016/0022236 A1 | 1/2016 | Ohishi | |

FOREIGN PATENT DOCUMENTS

| | | |
|---|---|---|
| JP | 2014-200339 | 10/2014 |
| JP | 2014-200593 | 10/2014 |
| JP | 2015-107171 | 6/2015 |
| JP | 2015-126868 | 7/2015 |

\* cited by examiner

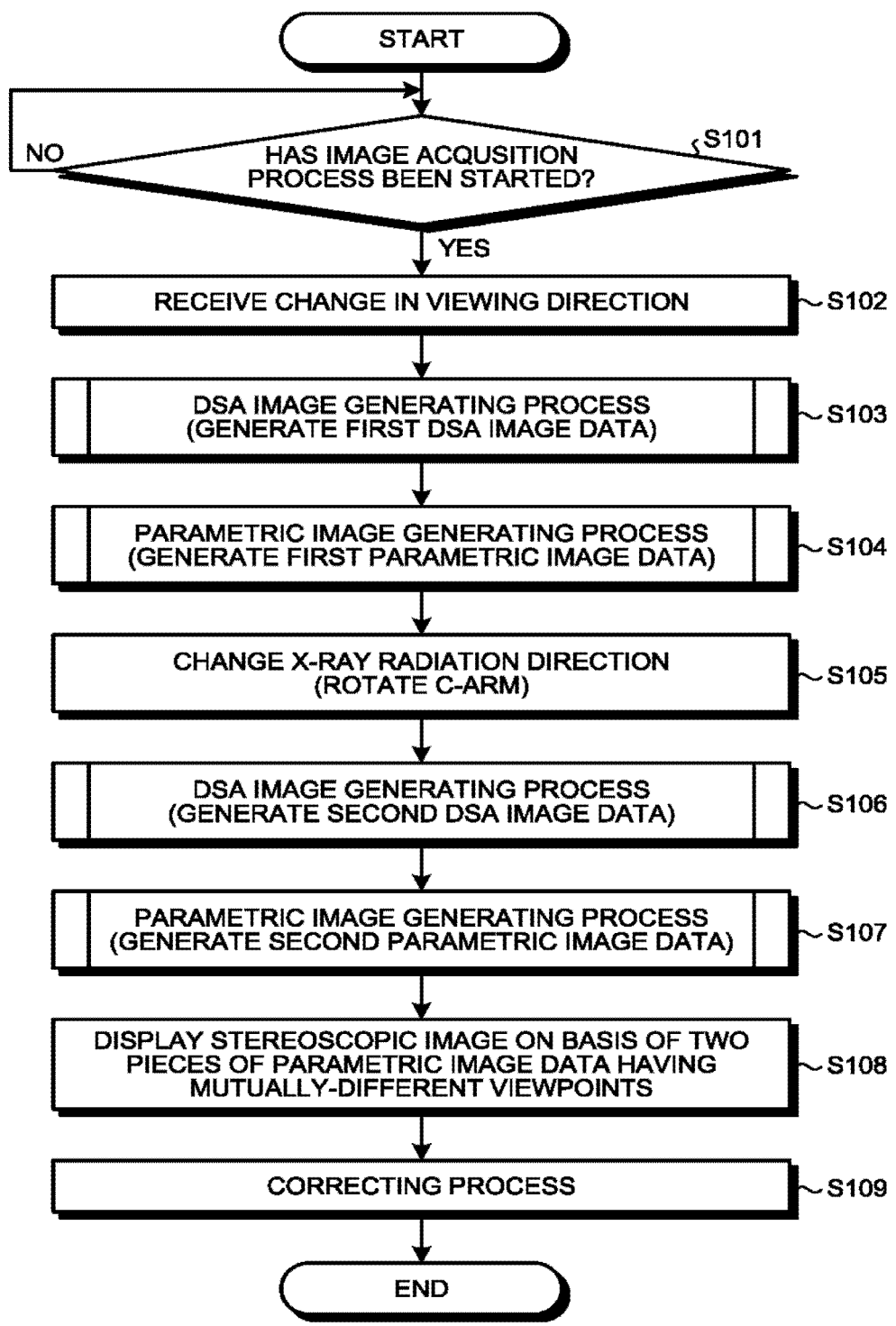

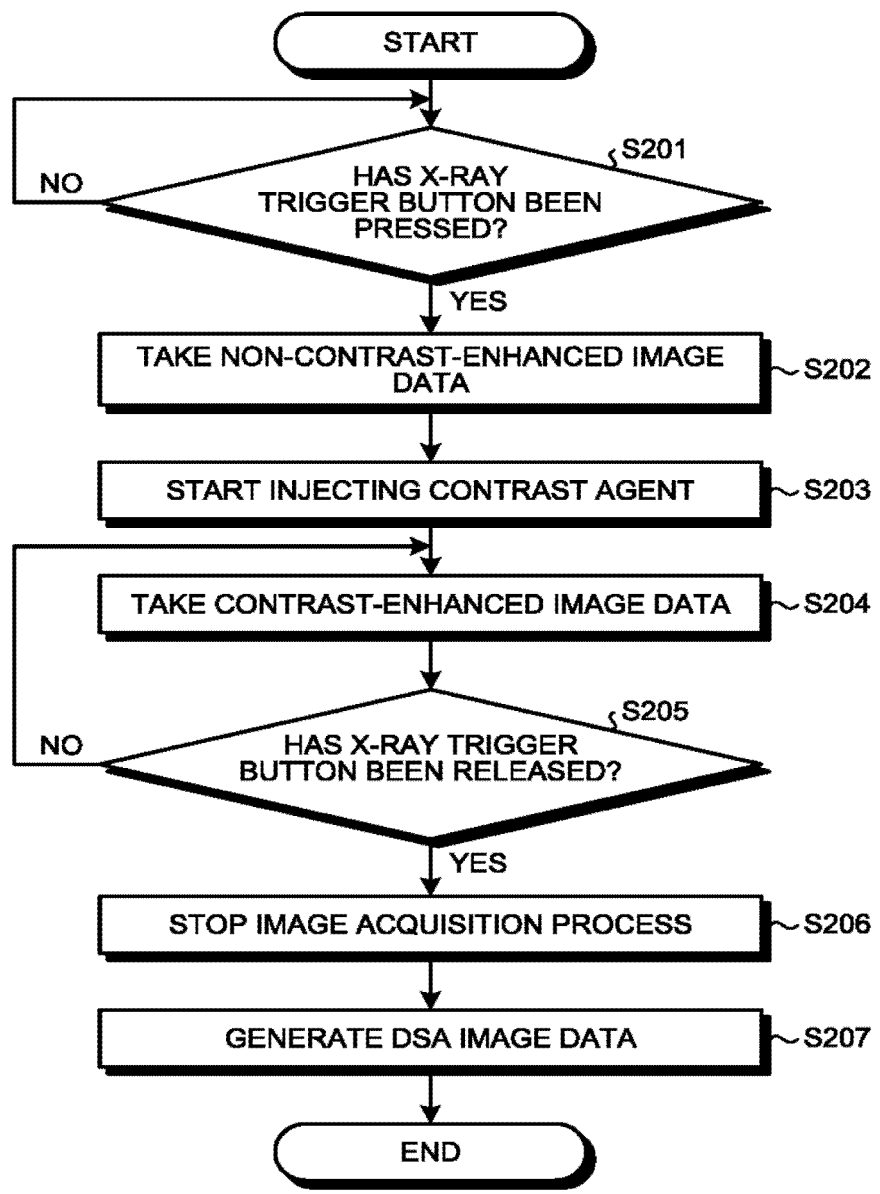

FIG.10
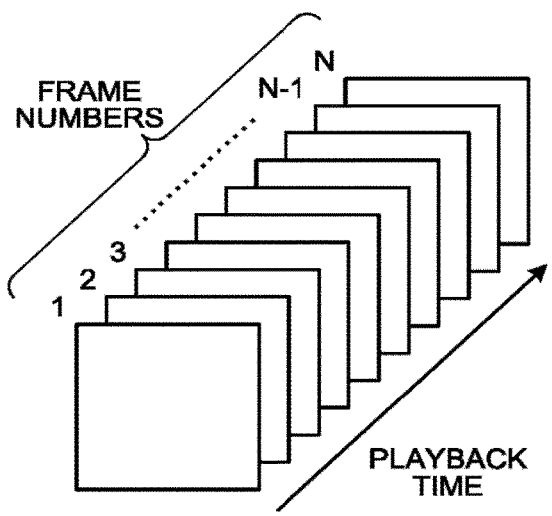
FIRST PARAMETRIC IMAGE DATA
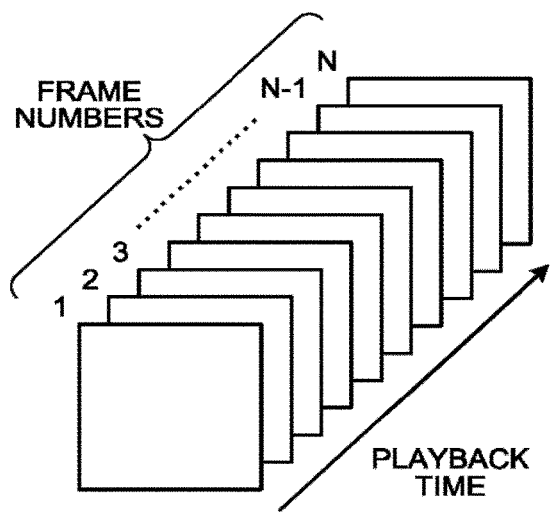
SECOND PARAMETRIC IMAGE DATA
FIG.11
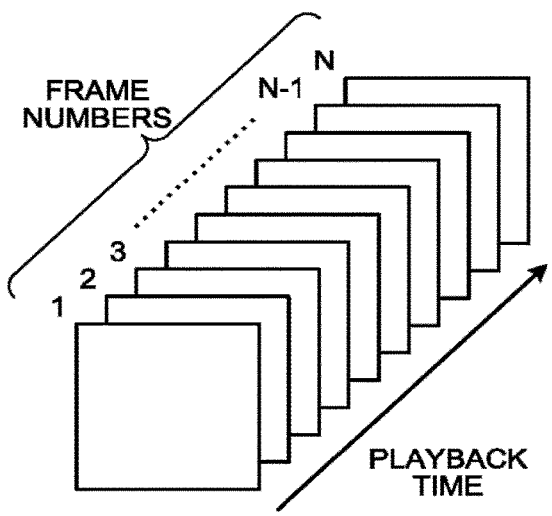
FIRST PARAMETRIC IMAGE DATA
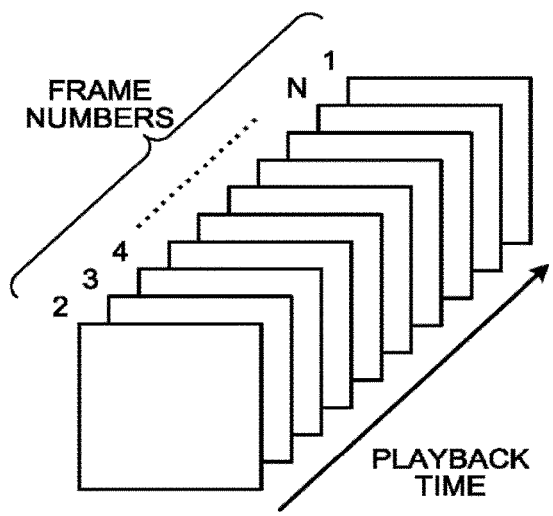
SECOND PARAMETRIC IMAGE DATA

X-RAY DIAGNOSIS APPARATUS, IMAGE PROCESSING APPARATUS, AND IMAGE DIAGNOSIS AIDING METHOD

CROSS-REFERENCE TO RELATED APPLICATIONS

This application is based upon and claims the benefit of priority from Japanese Patent Application No. 2016-127990, filed on Jun. 28, 2016; the entire contents of which are incorporated herein by reference.

FIELD

Embodiments described herein relate generally to an X-ray diagnosis apparatus, an image processing apparatus, and an image diagnosis aiding method.

BACKGROUND

Digital Subtraction Angiography (DSA) has conventionally been known as a method for imaging blood vessels by using an X-ray diagnosis apparatus. DSA is a technique used for obtaining image data selectively rendering blood vessels of which the contrast is enhanced by a contrast agent, by performing a subtraction on pieces of X-ray image data acquired before and after injecting the contrast agent to an examined subject (hereinafter, "patient"). For example, according to a DSA method, by performing an image acquisition process before injecting the contrast agent, a piece of X-ray image data in the absence of the contrast agent is acquired as mask image data. Further, by performing an image acquisition process while injecting the contrast agent, a piece of X-ray image data in the presence of the contrast agent is acquired as contrast image data. Further, DSA image data is generated by performing the subtraction between the mask image data and the contrast image data.

Further, another technique called parametric imaging is also known by which a parameter related to an inflow time of the contrast agent is expressed in an image, with the use of the DSA method described above. For example, during a parametric imaging process, changes in pixel value in each of different positions in the DSA image data are regarded as changes in concentration level of the contrast agent, so as to calculate a time at which a temporal change in the pixel value exhibits a peak value or a specific value as an inflow time. Further, during the parametric imaging process, parametric imaging image data (which hereinafter may be referred to as "parametric image data") is generated by mapping a color corresponding to the calculated inflow time onto each of the positions.

Further, for X-ray diagnosis apparatuses, various types of techniques have been proposed to provide X-ray image data that enables the viewer to have a stereoscopic view. For example, a technique is known by which parallax images for the right eye and the left eye are taken by varying the angle of a C-arm.

BRIEF DESCRIPTION OF THE DRAWINGS

FIG. 3 is a flowchart illustrating a processing procedure performed by the X-ray diagnosis apparatus according to the first embodiment;

FIG. 4 is a flowchart illustrating a processing procedure in a DSA image generating process according to the first embodiment;

FIG. 10 is a drawing for explaining a synchronization display realized by a display controlling function according to the first embodiment;

FIG. 11 is a drawing for explaining a frame number correcting process in a non-synchronization display mode according to the first embodiment;

DETAILED DESCRIPTION

An X-ray diagnosis apparatus of according to an embodiment includes processing circuitry. The processing circuitry is configured: to generate first subtraction image data by performing a subtraction on contrast-enhanced image data and non-contrast-enhanced image data each taken in a time series by using first image acquisition conditions, while using X-rays radiated from a first direction; and to generate second difference image data by performing a subtraction on contrast-enhanced image data and non-contrast-enhanced image data each taken in a time series by using second image acquisition conditions that are substantially the same as the first image acquisition conditions, while using X-rays radiated from a second direction. The processing circuitry is configured: to generate first color image data by using first processing condition, each pixel of the first color image data having a color according to a temporal transition at a corresponding position of the first subtraction image data; to generate second color image data by using second processing condition that is substantially same as the first processing condition, each pixel of the second color image data having a color according to a temporal transition at a corresponding position of the second subtraction image data. The processing circuitry is configured to cause a stereoscopic image to be displayed on the basis of the first color image data and the second color image data.

Exemplary embodiments of an X-ray diagnosis apparatus, an image processing apparatus, and an image diagnosis aiding method will be explained below, with reference to the accompanying drawings. Possible embodiments are not limited to the embodiments described below. Further, the description of each of the embodiments is, in principle, similarly applicable to any other embodiments.

First Embodiment

Figure 1:
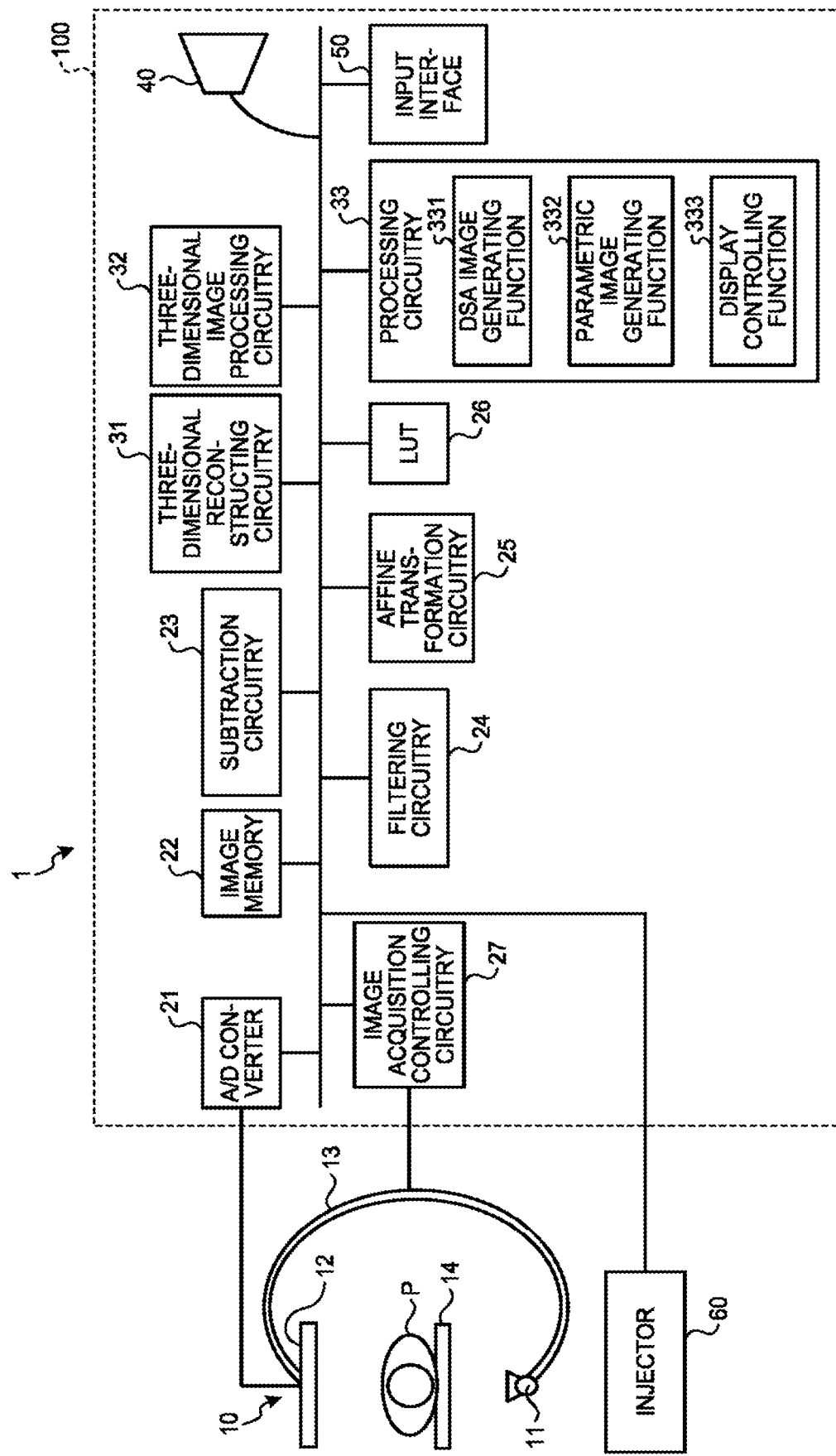
FIG. 1 is a diagram illustrating an exemplary configuration of an X-ray diagnosis apparatus according to a first embodiment.

FIG. 1 is a diagram illustrating an exemplary configuration of an X-ray diagnosis apparatus 1 according to a first embodiment. As illustrated in FIG. 1, the X-ray diagnosis apparatus 1 according to the first embodiment includes an X-ray image acquisition mechanism 10 and an image processing apparatus 100.

The X-ray image acquisition mechanism 10 includes an X-ray tube 11, a detector (a Flat Panel Detector [FPD]) 12, a C-arm 13, and a couch 14. An injector 60 is connected to the X-ray image acquisition mechanism 10.

The injector 60 is a device configured to inject a contrast agent through a catheter inserted in an examined subject (hereinafter, "patient") P. In this situation, an injection of the contrast agent from the injector 60 may be started according to an injection start instruction received via the image processing apparatus 100 (explained later) or may be started according to an injection start instruction that is directly input to the injector 60 by an operator such as a physician.

The C-arm 13 supports the X-ray tube 11 and the detector 12 configured to detect X-rays radiated from the X-ray tube 11. With the use of a motor (not illustrated), the C-arm 13 is configured to rotate, at a high speed like a propeller, around the patient P who is lying on the couch 14. In the present example, the C-arm 13 is supported so as to be rotatable with respect to X-, Y-, and Z-axes, which are three axes orthogonal to one another. The C-arm 13 is rotated by a driving unit (not illustrated) on each of the axes individually. The C-arm 13 is an example of a supporting machine.

Figure 2A:
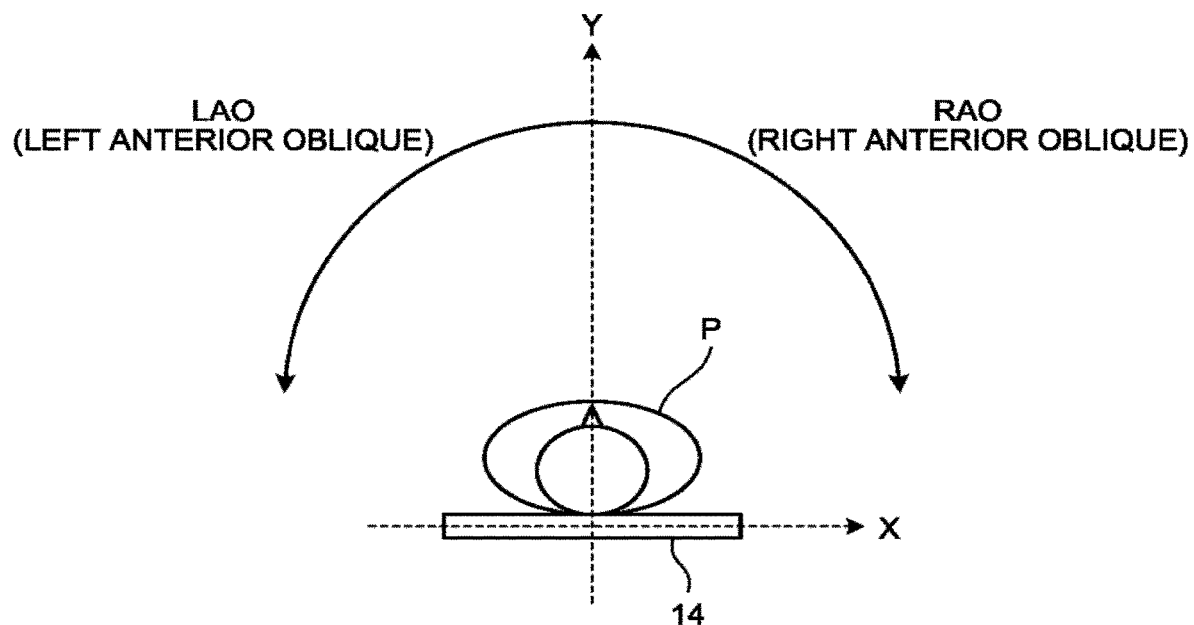
FIGS. 2A and 2B are drawings for explaining rotation directions of a C-arm according to the first embodiment.
Figure 2B:
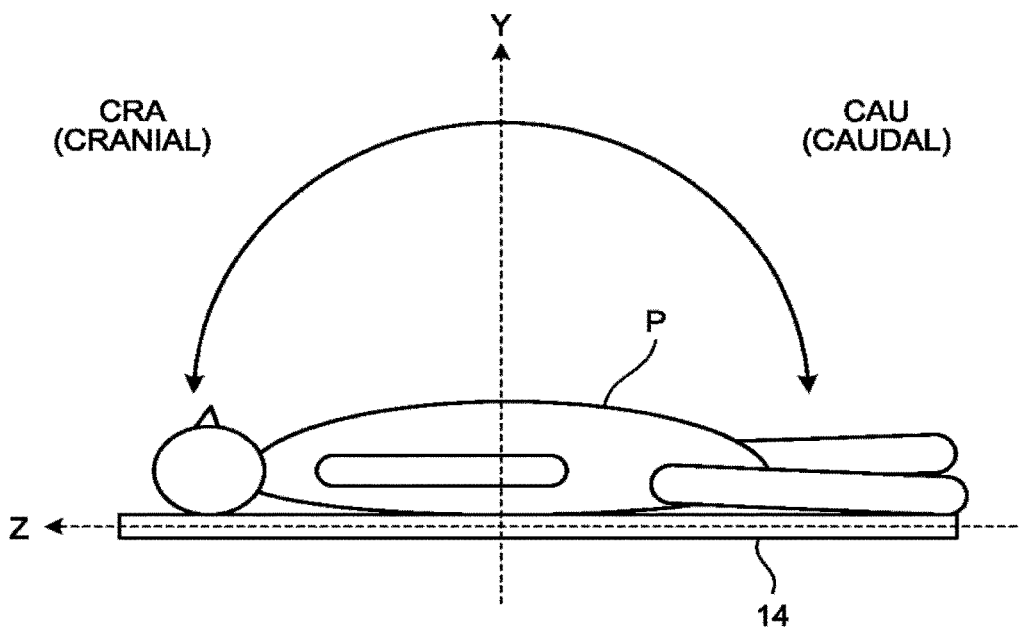

FIGS. 2A and 2B are drawings for explaining rotation directions of the C-arm 13 according to the first embodiment. FIG. 2A illustrates the patient P viewed from the positive direction on the Z-axis. FIG. 2B illustrates the patient P viewed from the positive direction on the X-axis.

As illustrated in FIG. 2A, while using the Y-axis indicating a frontal direction of the patient P as a reference, a rotation in the direction to the left-hand side of the patient P is referred to as a Left Anterior Oblique (LAO) rotation, whereas a rotation in the opposite direction of an LAO rotation is referred to as a Right Anterior Oblique (RAO) rotation. Further, as illustrated in FIG. 2B, while using the Y-axis indicating a frontal direction of the patient P as a reference, a rotation in the direction toward the cranium of the patient P is referred to as a cranial (CRA) rotation, whereas a rotation in the opposite direction of a CRA rotation is referred to as a caudal (CAU) rotation. For example, when the X-ray detector 12 is positioned in the positive direction on the Y-axis (i.e., in a straight-on position from the patient), the angle of the C-arm 13 is expressed as (RAO/LAO 0, CRA/CAU 0), which means that the RAO/LAO angle is 0 degrees, while the CRA/CAU angle is also 0 degrees.

The X-ray tube 11 is an X-ray source configured to generate X-rays by using the high voltage supplied thereto from a high-voltage generator (not illustrated). The detector 12 is a device in which a plurality of X-ray detecting elements are arranged in a matrix formation to detect X-rays that have passed through the patient P. The X-ray detecting elements included in the detector 12 are configured to output the X-rays that have passed through the patient P, to an Analog/Digital (A/D) converter 21 (explained later).

As illustrated in FIG. 1, the image processing apparatus 100 includes the Analog/Digital (A/D) converter 21, an image memory 22, subtraction circuitry 23, filtering circuitry 24, affine transformation circuitry 25, a Look Up Table (LUT) 26, image acquisition controlling circuitry 27, three-dimensional reconstructing circuitry 31, three-dimensional image processing circuitry 32, processing circuitry 33, a display 40, and an input interface 50.

The display 40 is configured to display various types of images processed by the image processing apparatus 100 and various types of information such as a Graphical User Interface (GUI). For example, the display 40 may be configured by using a Cathode Ray Tube (CRT) monitor, a liquid crystal monitor, or the like.

In the present example, the display 40 is a display device dedicated for stereoscopic viewing and is capable of displaying a stereoscopic image that enables the viewer to have a stereoscopic view on the basis of left-eye image data and right-eye image data. For example, the display 40 has a structure in which the display surface thereof has pasted thereon a lenticular sheet that appears to have a number of semi-cylindrical lenses arranged side by side or a fly-eye lens configured with a large number of lenses such as those in the eyes of a fly. Accordingly, as a result of trajectories of light beams being changed, the viewer is able to view a stereoscopic image with his/her own eyes without wearing stereoscopic viewing eyeglasses. In another example, the display 40 does not necessarily have to be a display device dedicated for eyeglass-free stereoscopic viewing. In that situation, the display 40 may be a display device that synchronizes with eyeglasses dedicated for stereoscopic viewing. While the left-eye image data is being displayed, only the left lens of the eyeglasses is transmitting light, and the right lens of the eyeglasses is not transmitting any light. Conversely, while the right-eye image data is being displayed, only the right lens of the eyeglasses is transmitting light, and the left lens of the eyeglass is not transmitting any light. In yet another example, the display 40 may have a structure in which the display surface thereof has pasted thereon a polarizing filter, so that, for example, horizontal polarization is applied to even-numbered pixel lines, while vertical polarization is applied to odd-numbered pixel lines. The left lens of a pair of stereoscopic viewing eyeglasses is configured to transmit only the horizontally-polarized light, while the right lens thereof is configured to transmit only the vertically-polarized light. Accordingly, the even-numbered pixel lines are configured to display the image data for the left eye, while the odd-numbered pixel lines are configured to display the image data for the right eye. In this manner, X-ray image data is displayed so as to enable the viewer to have a stereoscopic view while wearing eyeglasses dedicated for stereoscopic viewing.

The input interface 50 corresponds to an input device such as, for example, a mouse, a keyboard, a button, a panel switch, a touch command screen, a foot switch, a trackball, a joystick, and/or the like. The input interface 50 is configured to receive various types of instructions from the operator and to transfer the received various types of instructions to any of the circuits included in the image processing apparatus 100, as appropriate.

Further, for example, the input interface 50 includes an X-ray trigger button used for instructing that X-rays be radiated. When the X-ray trigger button is pressed by the operator, the X-ray diagnosis apparatus 1 starts an X-ray image data acquisition process. Further, for example, the input interface 50 includes an apparatus driving button used for instructing that the X-ray radiation direction be changed. When the apparatus driving button is pressed by the operator, the X-ray diagnosis apparatus 1 changes the X-ray radiation direction by rotating the C-arm 13 in a direction set in advance.

The A/D converter 21 is connected to the detector 12 and is configured to convert an analog signal input thereto from the detector 12 into a digital signal and to store the digital signal resulting from the conversion into the image memory 22 as X-ray image data.

The image memory 22 is configured to store therein the X-ray image data. Further, the image memory 22 is configured to store therein reconstructed data (volume data) reconstructed by the three-dimensional reconstructing circuitry 31 (explained later) and a three-dimensional image generated by the three-dimensional image processing circuitry 32. Also, the image memory 22 is capable of storing therein computer-executable programs.

The subtraction circuitry 23 is configured to generate difference image data such as Digital Subtraction Angiography (DSA) image data. For example, the subtraction circuitry 23 generates either DSA image data by using mask image data and contrast image data stored in the image memory 22 or volume data rendering a blood vessel structure by using two pieces of volume data. In the present example, the mask image data corresponds to X-ray image data (non-contrast-enhanced image data) taken before a contrast agent is injected. Further, the contrast image data corresponds to X-ray image data (contrast-enhanced image data) taken while a contrast agent is being injected.

The filtering circuitry 24 is configured to perform a spatial or temporal filtering process or the like. The affine transformation circuitry 25 is configured to enlarge, minify, and move images. The LUT 26 has stored therein tables used for performing a gray-scale level converting process.

The image acquisition controlling circuitry 27 is configured to control various types of processes related to image acquisition processes performed by the X-ray image acquisition mechanism 10, under control of the processing circuitry 33 explained later. For example, the image acquisition controlling circuitry 27 controls a rotation image acquisition process by which X-ray images are taken continuously at a predetermined frame rate while the C-arm 13 is being rotated. In one example, as being triggered by a signal output from the injector 60 when an injection of the contrast agent is started, the image acquisition controlling circuitry 27 controls the rotation image acquisition process of X-ray image data performed multiple times after a single injection of the contrast agent. In this situation, the image acquisition controlling circuitry 27 performs the rotation image acquisition processes in synchronization with times at which the contrast agent reaches the target to be imaged by the rotation image acquisition processes, by controlling the start of each of the rotation image acquisition processes performed multiple times, on the basis of an elapsed time period that starts being clocked at the start of the single injection of the contrast agent.

Further, while controlling the rotation of the C-arm 13, the image acquisition controlling circuitry 27 exercises control so that the X-ray tube 11 generates X-rays either continuously or intermittently by controlling the high-voltage generator (not illustrated) and so that the detector 12 detects the X-rays that have passed through the patient P. In this situation, the image acquisition controlling circuitry 27 causes the X-ray tube 11 to generate the X-rays, on the basis of an X-ray generation condition that is set by the processing circuitry 33 (explained later) for each of the rotation image acquisition processes.

The three-dimensional reconstructing circuitry 31 is configured to reconstruct the reconstructed data (the volume data) from the X-ray images acquired through the rotation image acquisition processes performed by the X-ray image acquisition mechanism 10. For example, the subtraction circuitry 23 generates DSA image data by subtracting, from the contrast image data acquired by rotational acquisition, the mask image data acquired by rotational acquisition, whose imaging angles are substantially the same as those of the contrast image data. The image memory 22 stores the DSA image data generated by the subtraction circuitry 23. The three-dimensional reconstructing circuitry 31 reconstructs the volume data including the blood vessel structure from the DSA image data stored in the image memory 22. Alternatively, the three-dimensional reconstructing circuitry 31 reconstructs pieces of volume data separately by using the rotation X-ray image data serving as the mask image data and the rotation X-ray image data serving as the contrast image data that are stored in the image memory 22 and further reconstructs the volume data rendering the blood vessel structure by performing a subtraction on the two pieces of volume data. After that, the three-dimensional reconstructing circuitry 31 stores the reconstructed volume data into the image memory 22.

The three-dimensional image processing circuitry 32 generates three-dimensional medical image data from the volume data stored in the image memory 22. For example, the three-dimensional image processing circuitry 32 generates volume rendering image data or Multi Planar Reconstruction (MPR) image data from the volume data. After that, the three-dimensional image processing circuitry 32 stores the generated three-dimensional medical image data into the image memory 22. Also, the three-dimensional image processing circuitry 32 performs a gray-scale level converting process on the three-dimensional medical image data, by referring to the LUT 26.

The processing circuitry 33 is configured to control the entirety of the X-ray diagnosis apparatus 1. More specifically, the processing circuitry 33 controls various types of process related to the X-ray image data acquisition process and the display image generating process performed by the X-ray image acquisition mechanism 10, as well as the display image displaying process performed by the display 40. For example, the processing circuitry 33 generates three-dimensional image data from the rotation image acquisition process performed by the X-ray image acquisition mechanism 10 and the X-ray image data taken by the rotation image acquisition processes and further causes the display 40 to display the generated three-dimensional image data.

Further, as illustrated in FIG. 1, the processing circuitry 33 is configured to execute a parametric image generating function 332 and a display controlling function 333. In this situation, for example, processing functions performed by the parametric image generating function 332 and the display controlling function 333 that are each a constituent element of the processing circuitry 33 illustrated in FIG. 1 are recorded in a storage device (e.g., the image memory 22) of the X-ray diagnosis apparatus 1 in the form of computer-executable programs. The processing circuitry 33 is a processor configured to realize the functions corresponding to the programs by reading and executing the programs from the storage device. In other words, the processing circuitry 33 that has read the programs has the functions illustrated within the processing circuitry 33 in FIG. 1.

The configuration illustrated in FIG. 1 is merely an example. For instance, FIG. 1 illustrates the plurality of circuits (the processors), namely, the subtraction circuitry 23, the filtering circuitry 24, the affine transformation circuitry 25, the image acquisition controlling circuitry 27, the three-dimensional reconstructing circuitry 31, the three-dimensional image processing circuitry 32, and the processing circuitry 33. However, these circuits do not necessarily have to be configured independently of one another. For example, arbitrary two or more of these circuits may be combined together, as appropriate.

The term "processor" used in the explanation above denotes, for example, a circuit such as a Central Processing Unit (CPU), a Graphics Processing Unit (GPU), an Application Specific Integrated Circuit (ASIC), or a programmable logic device (e.g., a Simple Programmable Logic Device [SPLD], a Complex Programmable Logic Device [CPLD], or a Field Programmable Gate Array [FPGA]). Each of the processors realizes the function thereof by reading the program stored in the storage and executing the read program. Alternatively, it is also acceptable to directly incorporate the program into the circuit of each of the processors, instead of having the programs stored in the storage. In that situation, each of the processors realizes the function thereof by reading the program incorporated in the circuit thereof and executing the read program. The processors according to the present embodiments each do not necessarily have to individually be configured as a single circuit. It is also acceptable to structure a single processor by combining together a plurality of independent circuits so as to realize the functions thereof. Further, it is also acceptable to integrate the plurality of constituent elements illustrated in each of the drawings into a single processor so as to realize the functions thereof.

The exemplary configuration of the X-ray diagnosis apparatus 1 according to the first embodiment has thus been explained. In the X-ray diagnosis apparatus 1 configured as described above, to provide an image that enables the viewer to have a stereoscopic view in a parametric imaging process, the processing circuitry 33 executes, a DSA image generating function 331, the parametric image generating function 332, and the display controlling function 333.

That is to say, the DSA image generating function 331 is configured to generate two pieces of DSA image data having mutually-different viewpoints in a time series by using substantially the same image acquisition conditions between the two. In other words, the DSA image generating function 331 generates first subtraction image data using contrast image data (contrast-enhanced image data) and mask image data (non-contrast-enhanced image data), each of the contrast image data and the mask image data being taken in a time series by using a first image acquisition condition with X-rays radiated in a first direction. And the DSA image generating function 331 generates second subtraction image data using contrast image data and mask image data, each of the contrast image data and the mask image data being taken, with X-rays radiated in a second direction, in a time series by using a second image acquisition condition that are substantially same as the first image acquisition condition. The DSA image generating function 331 is an example of a difference image generating unit. The DSA image data is an example of difference image data.

Subsequently, by using the two generated pieces of DSA image data, the parametric image generating function 332 generates two pieces of parametric image data having mutually-different viewpoints by using substantially the same processing conditions between the two. In this situation, the parametric image data expresses a parameter related to the inflow time of the contrast agent in an image. For example, the parametric image data is color image data in which a color corresponding to a temporal change in pixel value is assigned to each of different positions in the DSA image. In other words, the parametric image generating function 332 generates first color image data by using a first processing condition, each pixel of the first color image data having a color according to a temporal transition at a corresponding position of the first subtraction image data. And the parametric image generating function 332 generates, by using a second processing condition that is substantially same as the first processing condition, second color image data, each pixel of the second color image data having a color according to a temporal transition at a corresponding position of the second subtraction image data. The parametric image generating function 332 is an example of a color image generating unit.

After that, the display controlling function 333 causes a stereoscopic image to be displayed on the basis of the two generated pieces of parametric image data. As a result, the X-ray diagnosis apparatus 1 is able to provide an image that enables the viewer to have a stereoscopic view in the parametric imaging process.

In this situation, for example, the functions executed by the processing circuitry 33 may be set in advance as an image acquisition computer program used for the X-ray parametric imaging process (hereinafter, "X-ray parametric imaging-purpose image acquisition program"). For example, the X-ray parametric imaging-purpose image acquisition program has registered therein a parallax angle, in advance. The parallax angle is an angle used for determining the positions of two viewpoints that are set for realizing a stereoscopic view. Strictly speaking, the parallax angle varies depending on the distance between the left and the right eyeballs of the viewer who has the stereoscopic view. However, generally speaking, an angle in the range from 3 degrees to 5 degrees is considered to be an appropriate parallax angle. In the first embodiment, an example in which "5 degrees" is registered as the parallax angle will be explained; however, possible embodiments are not limited to this example. It is possible to set any arbitrary angle as the parallax angle. Alternatively, the parallax angle does not necessarily have to be set in advance and may arbitrarily be set every time an image acquisition process is performed, for example.

Further, the X-ray parametric imaging-purpose image acquisition program has registered therein, in advance, image acquisition conditions used for acquiring contrast-enhanced image data and non-contrast-enhanced image data, as well as processing conditions for generating the parametric image data. The image acquisition conditions and the processing conditions will be explained later.

FIG. 3 is a flowchart illustrating a processing procedure performed by the X-ray diagnosis apparatus 1 according to the first embodiment. The processing procedure illustrated in FIG. 3 is started when, for example, the operator inputs an instruction indicating that the process of the X-ray parametric imaging-purpose image acquisition program should be started.

As illustrated in FIG. 3, the processing circuitry 33 judges whether an image acquisition process has been started (step S101). For example, when the operator has input an instruction indicating that the process of the X-ray parametric imaging-purpose image acquisition program should be started, the processing circuitry 33 determines that an image acquisition process has been started and executes the process at step S102 and thereafter. Also, at this time, the processing circuitry 33 communicates with the injector 60 so as to prepare for a contrast agent injecting process. On the contrary, when the judgment result at step S101 is in the negative, the processing circuitry 33 does not start the image acquisition process, and the processes described below are in a stand-by state.

Subsequently, the processing circuitry 33 receives a change in the viewing direction (step S102). In this situation, the viewing direction corresponds to the angular direction of the parallax between an image acquisition process performed the first time (hereinafter, "first-time image acquisition process") and an image acquisition process performed the second time (hereinafter, "second-time image acquisition process"). For example, as the viewing direction, "patient's left/right direction" or "patient's head/toe direction" may be set. For example, the "patient's left/right direction" denotes that the C-arm 13 is rotated so that the position of the X-ray tube 11 moves in the left/right direction (RAO/LAO) of the patient (the patient P) during the transition from the first-time image acquisition process to the second-time image acquisition process. For example, the "patient's head/toe direction" denotes that the C-arm 13 is rotated so that the position of the X-ray tube 11 moves in the head/toe direction (CRA/CAU) of the patient during the transition from the first-time image acquisition process to the second-time image acquisition process.

For example, the X-ray parametric imaging-purpose image acquisition program has configured therein the "patient's left/right direction" as a default viewing direction. Further, the processing circuitry 33 receives a change in the viewing direction within a number of seconds after the operator inputs the instruction indicating that the process of the X-ray parametric imaging-purpose image acquisition program should be started. During the time period of a number of seconds (approximately 5 seconds to 10 seconds), when the operator inputs an instruction indicating that the viewing direction should be changed to "patient's head/toe direction" via the input device such as a mouse or a keyboard, the processing circuitry 33 changes the viewing direction from the default viewing direction to the viewing direction designated by the operator. In contrast, when the operator inputs no instruction indicating that the viewing direction should be changed during the time period of a number of seconds, the processing circuitry 33 performs the processes described below by using the default viewing direction. In the present example, the situation is explained in which either the "patient's left/right direction" or the "patient's head/toe direction" is set as the viewing direction; however, possible embodiments are not limited to this example. It is possible to set any arbitrary direction as the viewing direction.

It should be noted that it is desirable to determine the viewing direction (the angular direction of the parallax) in accordance with the direction in which the blood vessel extends (hereinafter, "extending direction of the blood vessel"). For example, when the blood vessel subject to the viewing extends in the patient's head/toe direction, it is desirable to set the viewing direction to be the "patient's left/right direction". In contrast, when the blood vessel subject to the viewing extends in the patient's left/right direction, it is desirable to set the viewing direction to be the "patient's head/toe direction". The reasons is that, when the viewing direction is substantially parallel to the extending direction of the blood vessel, a stereoscopic image displayed for the purpose of realizing a stereoscopic view may not be viewed stereoscopically or may appear blurry, in some situations. For this reason, it is desirable to set the viewing direction so as to be as closest as possible to being orthogonal to the extending direction of the blood vessel, instead of being parallel thereto. Alternatively, the processing circuitry 33 may automatically determine the viewing direction in accordance with the extending direction of the blood vessel. The process performed by the processing circuitry 33 in that situation will be explained later.

At step S103, the DSA image generating function 331 performs a DSA image generating process. The DSA image generating process performed at step S103 is a process to generate DSA image data from the first-time image acquisition process (which hereinafter may be referred to as "first DSA image data").

For example, the DSA image generating function 331 performs the DSA image generating process after moving the X-ray tube 11 to the position from which the X-rays are radiated (the radiation position). For example, the operator performs an operation to designate the X-ray radiation position to be a lateral side of the patient (LAO 90, CRA/CAU 0). In response to this operation, the DSA image generating function 331 moves the X-ray tube 11 to the position on the lateral side of the patient (LAO 90, CRA/CAU 0) by rotating the C-arm 13 and starts the DSA image generating process. In the present example, the situation is explained in which the X-ray radiation position for the first-time image acquisition process is designated by the operator; however, possible embodiments are not limited to this example. For instance, a default radiation position may be set in advance as the X-ray radiation position. Alternatively, the X-ray radiation position may be determined on the basis of the region of interest, the parallax angle, the angular direction of the parallax, and/or the like.

FIG. 4 is a flowchart illustrating a processing procedure in the DSA image generating process according to the first embodiment. The processing procedure in the DSA image generating process illustrated in FIG. 4 corresponds to the process at step S103 illustrated in FIG. 3.

As illustrated in FIG. 4, the DSA image generating function 331 receives pressing of the X-ray trigger button (step S201). For example, when the operator has pressed the X-ray trigger button (step S201: Yes), the DSA image generating function 331 causes the X-ray tube 11 to radiate X-rays and starts the processes at step S202 and thereafter. In the first embodiment, an example will be explained in which an X-ray image acquisition process is performed while the pressing of the X-ray trigger button at step S201 is being continued (i.e., while being long-pressed). In other words, the operator adjusts the image acquisition time period and the number of frames to be taken by arbitrarily changing the time period for which the X-ray trigger button is long-pressed. In this situation, until the X-ray trigger button is pressed (step S201: No), the DSA image generating function 331 does not start the processes at step S202 and thereafter.

The image acquisition conditions used in the processes of acquiring the contrast-enhanced image data and the non-contrast-enhanced image data, which are each started by the pressing of the X-ray trigger button, are registered, in advance, in the X-ray parametric imaging-purpose image acquisition program explained above. The image acquisition conditions registered in this situation include image acquisition conditions registered in advance in conventional image acquisition programs such as, for example, a target incident dose to determine an appropriate image level (to set a desired image noise level), a target X-ray tube voltage to achieve an appropriate X-ray acquiring condition, a tolerance range for the X-ray tube voltage, a tolerance range for the pulse width, options for the size of the X-ray focal point, and the like.

Subsequently, the DSA image generating function 331 acquires non-contrast-enhanced image data (step S202). For example, the DSA image generating function 331 acquires the non-contrast-enhanced image data representing a predetermined number of images (i.e., one or more images). The DSA image generating function 331 stores the acquired non-contrast-enhanced image data into the image memory 22.

After that, the DSA image generating function 331 causes the injection of a contrast agent to start (step S203). For example, the DSA image generating function 331 transmits an injection start signal to the injector 60 to instruct that the injection of the contrast agent be started. When having received the injection start signal transmitted thereto from the DSA image generating function 331, the injector 60 starts the injection of the contrast agent.

Subsequently, the DSA image generating function 331 acquires contrast-enhanced image data (step S204). For example, when a predetermined period of time has elapsed since the start of the injection of the contrast agent, the DSA image generating function 331 starts the contrast-enhanced image data acquisition process. Further, until the X-ray trigger button is released (step S205: No), the DSA image generating function 331 continuously acquires pieces of contrast-enhanced image data in a time series. Every time a piece of contrast-enhanced image data is taken, the DSA image generating function 331 stores the acquired piece of contrast-enhanced image data into the image memory 22. When having received a release of the X-ray trigger button (step S205: Yes), the DSA image generating function 331 stops the contrast-enhanced image data acquisition process (step S206).

After that, the DSA image generating function 331 generates DSA image data (step S207). For example, the DSA image generating function 331 generates a plurality of frames of DSA image data in a time series, by subtracting non-contrast-enhanced image data from each of the plurality of frames of contrast-enhanced image data that were continuously taken in the time series. In this situation, for the purpose of noise suppression, it is desirable when the non-contrast-enhanced image data used in the subtraction is image data obtained by calculating an arithmetic mean (or a bottom trace) of the non-contrast-enhanced image data representing the plurality of images. However, the non-contrast image data may image data representing an arbitrary single image. Further, the generated DSA image data (or the contrast-enhanced image data) may be displayed on the display 40, as appropriate.

In this manner, the DSA image generating function 331 generates the plurality of frames of DSA image data (the first DSA image data) in the time series. After that, the DSA image generating function 331 outputs the generated plurality of frames of DSA image data to the parametric image generating function 332.

The processing procedure illustrated in FIG. 4 described above is merely an example. Possible embodiments are not limited to the example illustrated in FIG. 4. For instance, the processing procedure in FIG. 4 does not necessarily have to be performed in the order described above. For instance, the process of generating the DSA image data (step S207) does not necessarily have to be performed after the image acquisition process is stopped (step S206). For example, the DSA image generating function 331 may sequentially generate pieces of DSA image data by subtracting the non-contrast-enhanced image from a different one of the pieces of contrast-enhanced image data, every time each of the pieces of contrast-enhanced image data is taken in the time series.

As another example, the image acquisition process may be stopped not by the releasing of the X-ray trigger button, but by pressing of the X-ray trigger button again, for example. In that situation, the X-ray trigger button does not need to be long-pressed at step S201. Alternatively, the image acquisition process may be stopped by pressing another button dedicated for stopping the image acquisition processes.

Returning to the description of FIG. 3, the parametric image generating function 332 performs a parametric image generating process (step S104). In this situation, the parametric image generating process at step S104 is a process to generate parametric image data from the first-time image acquisition process (which hereinafter may be referred to as "first parametric image data").

Figure 5:
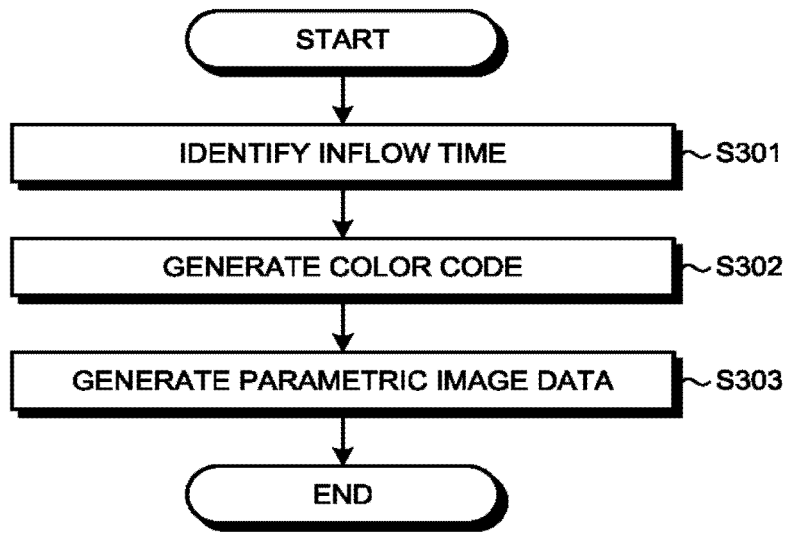
FIG. 5 is a flowchart illustrating a processing procedure in a parametric image generating process according to the first embodiment.

FIG. 5 is a flowchart illustrating a processing procedure in the parametric image generating process according to the first embodiment. The processing procedure in the parametric image generating process illustrated in FIG. 5 corresponds to the process at step S104 illustrated in FIG. 3.

As illustrated in FIG. 5, the parametric image generating function 332 identifies an inflow time (step S301). In this situation, the inflow time is a parameter defined on the basis of a temporal change in each of the pixel values, while regarding the change in pixel value in each of different positions in the DSA image data as a change in concentration level of the contrast agent. As a method for identifying the inflow time, an arbitrary one may be selected from a Time-to-Peak (TTP) method and a Time-to-Arrival (TTA) method. For example, according to the TTP method, a time at which the temporal change of the pixel value is at a maximum is identified as the inflow time. As another example, according to the TTA method, either a time at which the temporal change of the pixel value reaches a predetermined value or a time at which the temporal change of the pixel value reaches a predetermined percentage of the maximum value for the temporal change of the pixel value is identified as the inflow time.

Figure 6:
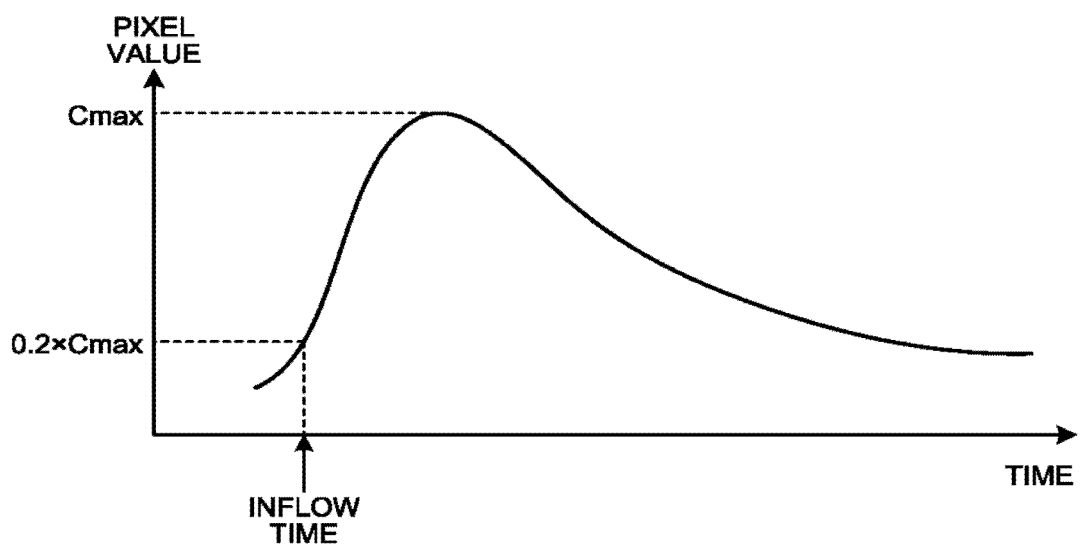
FIG. 6 is a drawing for explaining a process performed by a parametric image generating function according to the first embodiment.

FIG. 6 is a drawing for explaining a process performed by the parametric image generating function 332 according to the first embodiment. FIG. 6 illustrates a time-concentration profile analyzed with respect to an arbitrary pixel included in the DSA image data. In FIG. 6, the horizontal axis corresponds to time (the image acquisition period of the contrast-enhanced image data), whereas the vertical axis corresponds to the pixel value. With reference to FIG. 6, an example will be explained in which the TTA method is used as the method for identifying the inflow time.

As illustrated in FIG. 6, for example, the parametric image generating function 332 identifies an inflow time by analyzing the time-concentration profile, with respect to each of the pixels included in the DSA image data generated by the DSA image generating function 331. In the example illustrated in FIG. 6, the parametric image generating function 332 identifies a time at which the pixel value reaches 20% (0.2×Cmax) of the maximum pixel value (Cmax) as the inflow time at each pixel.

The illustration of FIG. 6 is merely an example, and possible embodiments are not limited to the example in FIG. 6. For instance, although FIG. 6 illustrates the example in which the percentage for identifying the inflow time by using the TTA method is set to "20%", possible embodiments are not limited to this example. It is acceptable to use an arbitrary percentage (or an arbitrary value). Also, the method for identifying the inflow time does not necessarily have to be the TTA method and may be the TTP method.

Subsequently, the parametric image generating function 332 generates one or more color codes (step S302). For example, when generating the parametric image data as a still image, the parametric image generating function 332 generates one color code. Alternatively, when generating the parametric image data as a dynamic image, the parametric image generating function 332 generates color codes of which the quantity corresponds to the number of frames included in the dynamic image. In the following sections, the color code generating process for generating a still image and the color code generating process for generating a dynamic image will sequentially be explained. As for a generating condition used for generating the one or more color codes, a default condition is set in advance; however, the generating condition may be set by the operator, as appropriate.

Figure 7A:
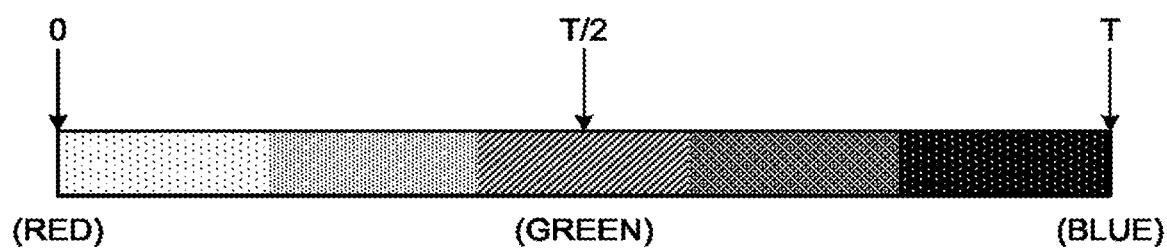
FIGS. 7A and 7B are drawings for explaining a color code generating process for generating a still image according to the first embodiment.
Figure 7B:
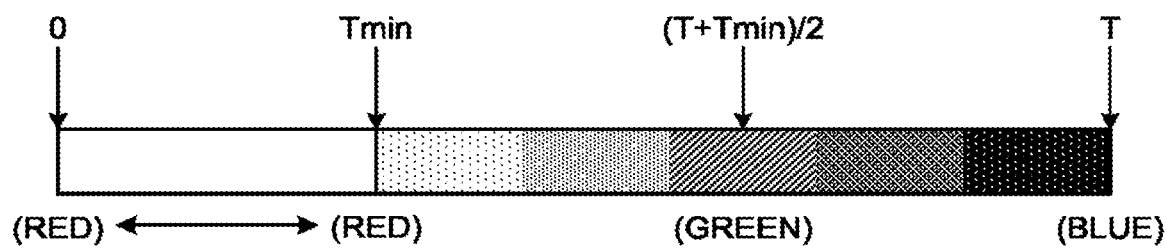

FIGS. 7A and 7B are drawings for explaining the color code generating process for generating a still image according to the first embodiment. FIGS. 7A and 7B illustrate examples in which the method for identifying the inflow time is the TTA method. According to the TTA method, the cycle and an initial value of the color code are each set to "Auto" as a default value. In this situation, "Auto" denotes that each of the values is automatically set in accordance with the acquisition time period (the image acquisition time period) of the DSA image data.

As illustrated in FIG. 7A, for example, when the acquisition time period of the DSA image data is from 0 seconds to T seconds, the parametric image generating function 332 sets the cycle of the color code to "T" and sets the initial value of the color code to "0". The color code is defined so as to display "red" when the inflow time t is equal to "0", to gradually change from "red" to "green" while the inflow time t is ranging from "0" to "T/2", and to display "green" when the inflow time is equal to "T/2". Further, the color code is defined so as to gradually change from "green" to "blue" while the inflow time t is ranging from "T/2" to "T", and to display "blue" when the inflow time is equal to "T".

As another example, as illustrated in FIG. 7B, a minimum value "Tmin" among the inflow times of all the pixels included in the DSA image data may be used as an initial value of the color code. This color code is defined so as to display "red" when the inflow time t is equal to "Tmin", to gradually change from "red" to "green" while the inflow time t is ranging from "Tmin" to "(T+Tmin)/2", and to display "green" when the inflow time t is equal to "(T+Tmin)/2". Further, this color code is defined so as to gradually change from "green" to "blue" while the inflow time t is ranging from "(T+Tmin)/2" to "T", and to display "blue" when the inflow time t is equal to "T". In this situation, in the color code illustrated in FIG. 7B, because red is assigned to the range from "0" to "Tmin", the color changes more significantly with respect to changes in the inflow time. For this reason, the color code illustrated in FIG. 7B is considered to be more suitable for rendering small changes in the inflow time.

As explained above, the parametric image generating function 332 generates the color code for the still image. The illustrations of FIGS. 7A and 7B are merely examples, and possible embodiments are not limited to the examples in FIGS. 7A and 7B. For instance, although FIGS. 7A and 7B illustrate the examples in which the TTA method is used as the method for identifying the inflow time, possible embodiments are not limited to these examples. The identifying method may be the TTP method. Further, the order of the colors defined in the color code is not limited to the examples illustrated in FIGS. 7A and 7B and may arbitrarily be set.

Figure 8:
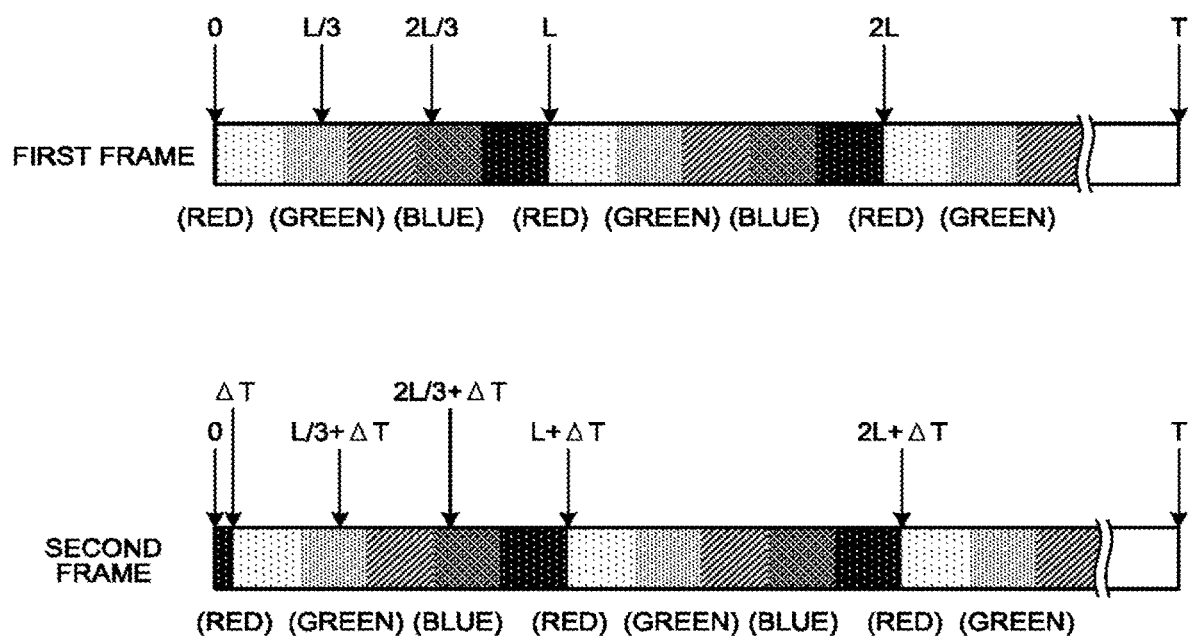
FIG. 8 is a drawing for explaining a color code generating process for generating a moving image according to the first embodiment.

FIG. 8 is a drawing for explaining the color code generating process for generating a dynamic image according to the first embodiment. With reference to FIG. 8, an example will be explained in which the generation method used for generating parametric image data as a dynamic image is a Circular Color Coding (CCC) method. The method for identifying the inflow time to be used with the CCC method may be either the TTA method or the TTP method.

As illustrated in FIG. 8, for example, when the acquisition time period of the DSA image data is from 0 seconds to T seconds, the parametric image generating function 332 sets the cycle of the color code to "L (where L<T)", the initial value of the color code to "0", and steps of the color code to "ΔT". After that, the parametric image generating function 332 generates color codes of which the quantity corresponds to the number of frames included in the dynamic image. For example, when the number of frames in the dynamic image is "N", the parametric image generating function 332 generates the color codes of which the quantity is equal to N, in correspondence with the first frame to an N-th frame.

For example, the color code corresponding to the first frame is defined so as to display "red" when the inflow time t is equal to "0", to gradually change from "red" to "green" while the inflow time t is ranging from "0" to "L/3", and to display "green" when the inflow time t is equal to "L/3". Further, the color code corresponding to the first frame is defined so as to gradually change from "green" to "blue" while the inflow time t is ranging from "L/3" to "2L/3", and to display "blue" when the inflow time t is equal to "2L/3". Further, the color code corresponding to the first frame is defined so as to gradually change from "blue" to "red" while the inflow time t is ranging from "2L/3" to "L", and to return to displaying "red" when the inflow time t is equal to "L". As explained herein, the color code corresponding to the first frame changes "red→green→blue→red" while the inflow time t changes from "0" to "L". Further, after the inflow period t reaches "L", the changes in the color from "0" to "L" are repeated. In other words, the color code corresponding to the first frame is defined so as to change "red→green→blue→red" while the inflow time t changes from "L" to "2L". Also, the color code corresponding to the first frame is defined so as to change "red→green→blue→red" while the inflow time t changes from "2L" to "3L". After that, similarly, the color code corresponding to the first frame is defined so as to change "red→green→blue→red" until the inflow time t reaches "T".

The color code corresponding to the second frame is generated by shifting the color code corresponding to the first frame by "ΔT". For example, the color code corresponding to the second frame is defined so as to display "red" when the inflow time t is equal to "Δt", to gradually change from "red" to "green" while the inflow time t is ranging from "Δt" to "L/3+Δt", and to display "green" when the inflow time t is equal to "L/3+Δt". Further, the color code corresponding to the second frame is defined so as to gradually change from "green" to "blue" while the inflow time t is ranging from "L/3+Δt" to "2L/3+Δt", and to display "blue" when the inflow time t is equal to "2L/3+Δt". Further, the color code corresponding to the second frame is defined so as to gradually change from "blue" to "red" while the inflow time t is ranging from "2L/3+Δt" to "L+Δt", and to return to displaying "red" when the inflow time t is equal to "L+Δt". Similarly to the color code corresponding to the first frame, the changes in the color from "ΔT" to "L+ΔT" are repeated several times, after the inflow time t reaches "L+Δt". Moreover, the color code corresponding to the second frame is defined so as to gradually change from "blue" to "red" while the inflow time t is ranging from "Δt−L/3" to "Δt", and to display "blue" when the inflow time t is equal to "Δt−L/3".

That is to say, the color code corresponding to the N-th frame is generated by shifting the color code corresponding to the (N−1)th frame by "ΔT". In other words, the color code corresponding to the N-th frame is generated by shifting the color code corresponding to the first frame by "ΔT×(N−1)".

The configuration illustrated in FIG. 8 is merely an example, and possible embodiments are not limited to the example in FIG. 8. For instance, the order of the colors defined in each of the color codes is not limited to the example illustrated in FIG. 8 and may arbitrarily be set.

In the manner described above, as the color codes for generating the dynamic image, the parametric image generating function 332 generates the color codes of which the quantity corresponds to the number of frames in the dynamic image. It is considered that each of the color codes used for generating the dynamic image is a cyclic color code that defines the cyclic change of the colors in response to the changes in the inflow time. The processing conditions used in the parametric image generating process are registered in advance in the X-ray parametric imaging-purpose image acquisition program described above. The registered processing conditions in this situation include, for example, a method for identifying the inflow time, the cycles of the color codes, phases of the color codes, initial values of the color codes, and information indicating whether the image is a still image or a dynamic image.

Returning to the description of FIG. 5, the parametric image generating function 332 generates parametric image data (step S303). For example, the parametric image generating function 332 generates the parametric image data by assigning a color corresponding to a temporal change in the pixel value, to each of the pixels in the DSA image data.

Figure 9:
FIG. 9 is a drawing for explaining another process performed by the parametric image generating function according to the first embodiment.

FIG. 9 is a drawing for explaining another process performed by the parametric image generating function 332 according to the first embodiment. FIG. 9 illustrates parametric image data rendering blood vessels in the brain of the patient P.

As illustrated in FIG. 9, for example, the parametric image generating function 332 generates the parametric image data by referring to the one or more color codes generated at step S302 and assigning the color corresponding to the inflow time of each of the pixels.

More specifically, the parametric image generating function 332 generates the parametric image data for the still image. For example, the parametric image generating function 332 generates the parametric image data by referring to the color code for the still image illustrated in FIG. 7A (or FIG. 7B) and assigning the color corresponding to the inflow time of each of the pixels.

Alternatively, the parametric image generating function 332 generates the parametric image data for the dynamic image. For example, the parametric image generating function 332 generates pieces of parametric image data of which the quantity corresponds to the number of frames included in the dynamic image, by referring to the color codes for the dynamic image illustrated in FIG. 8. More specifically, the parametric image generating function 332 generates a piece of parametric image data for the first frame by assigning a color corresponding to the inflow time of each of the pixels on the basis of the color code corresponding to the first frame. Further, the parametric image generating function 332 generates a piece of parametric image data for the second frame by assigning a color corresponding to the inflow time of each of the pixels on the basis of the color code corresponding to the second frame. In this manner, the parametric image generating function 332 generates a piece of parametric image data for an N-th frame, by assigning the color corresponding to the inflow time of each of the pixels, on the basis of the color code corresponding to the N-th frame.

Although the colors assigned in accordance with the inflow times were explained with reference to FIG. 9, it is desirable to further adjust the luminosity (the brightness level) on the basis of a maximum pixel value of each of the pixels. For example, it is desirable to arrange the luminosity of each of the pixels to be equal to "D/Dmax", which is a ratio of the maximum pixel value "D" of the pixel to the maximum pixel value "Dmax" among all the pixels included in the DSA image data.

In this manner, the parametric image generating function 332 generates the parametric image data (the first parametric image data) of either the still image or the dynamic image. After that, the parametric image generating function 332 outputs the generated parametric image data to the display controlling function 333.

Returning to the description of FIG. 3, the processing circuitry 33 changes the X-ray radiation direction (step S105). For example, by using the parallax angle and the angular direction (the viewing direction) of the parallax that are set in advance, the DSA image generating function 331 derives an X-ray radiation position for the second-time image acquisition process. In this situation, for example, the parallax angle is "5 degrees", while the angular direction of the parallax is the viewing direction set in the process at step S102 and is, for example, the "patient's left/right direction".

For example, when the X-ray radiation position in the first-time image acquisition process was a lateral side of the patient (LAO 90, CRA/CAU 0), the X-ray radiation position for the second-time image acquisition process may be selected from the following two candidates: (LAO 85, CRA/CAU 0) and (LAO 95, CRA/CAU 0). In this situation, the DSA image generating function 331 is capable of automatically selecting one of the two candidates according to a certain algorithm. For example, the DSA image generating function 331 changes the viewing direction to the right side (in the RAO positive direction) for an angle between (RAO 0) and (RAO 180) and to the left side (in the LAO positive direction) for an angle between (LAO 0) and (LAO 180). It should be noted that, when it is not possible to mechanically rotate the C-arm 13, the DSA image generating function 331 automatically changes the viewing direction to the opposite direction.

Further, the process of changing the X-ray radiation direction may be realized by, for example, half-pressing the X-ray trigger button. For example, while the operator is half-pressing the X-ray trigger button, the DSA image generating function 331 rotates the C-arm 13 in the angular direction of the parallax (i.e., the "patient's left/right direction") by the parallax angle (i.e., "5 degrees"). As a result, for example, the DSA image generating function 331 moves the X-ray tube 11 to the position expressed as (LAO 95, CRA/CAU 0). In this situation, the DSA image generating function 331 moves the X-ray tube 11 without changing the Source Image Distance (SID), the position of the collimator, the type or the thickness of the beam filter, or the position of a compensation filter. Alternatively, the DSA image generating function 331 may move the X-ray tube 11 as being triggered by the pressing of the apparatus driving button, for example, instead of by the half-pressing of the X-ray trigger button.

In the present example, the situation is explained in which the region of interest substantially coincides with the rotation center of the C-arm 13; however, possible embodiments are not limited to this example. For instance, when the region of interest is different from the rotation center of the C-arm 13, the position and the size of the region of interest rendered in the parallax image (the parametric image data) will be different; however, it is possible to arrange the position and the size to be the same by performing an image processing process (a parallel translation, an enlarging/minifying process, or the like) on the parallax image. Further, it is also possible to increase a magnification ratio of an X-ray optical system by bringing the region of interest closer to the X-ray tube 11. This process will be explained later.

Subsequently, the DSA image generating function 331 performs a DSA image generating process (step S106). The DSA image generating process at step S106 is a process to generate DSA image data from the second-time image acquisition process (which hereinafter may be referred to as "second DSA image data").

In this situation, except that the image acquisition process is performed in the X-ray radiation direction changed at step S105, the DSA image generating function 331 performs the second-time DSA image generating process by using substantially the same image acquisition conditions as the image acquisition conditions used for the first-time DSA image generating process. In other words, the DSA image generating function 331 generates the first DSA image data and the second DSA image data by using substantially the same image acquisition conditions between the two, with respect to the injection condition of the contrast agent, the X-ray radiation condition, the size of the Field Of View (FOV) radiated by the X-rays, the distance (the SID) between the focal point of the X-ray tube 11 that radiates the X-rays and the X-ray detector, the position of the couch 14, and the rotation center (an Iso-Center) of the C-arm 13. Further, the DSA image generating function 331 generates the first DSA image data and the second DSA image data by using substantially the same injection conditions between the two, with respect to the time period from the time when the injection of the contrast agent is started to the time when the contrast-enhanced image data acquisition process is started, the injection speed of the contrast agent, the pressure applied to the injector of the injected agent, and the rising curve before reaching the expected injection speed. Further, the DSA image generating function 331 generates the first DSA image data and the second DSA image data by using substantially the same radiation conditions between the two, with respect to the frame rate of the images acquired by using the X-rays, the X-ray tube voltage of the X-ray tube 11, the X-ray tube current of the X-ray tube 11, the X-ray pulse width, the position of the collimator for the X-ray tube 11, the type and the thickness of the beam filter for the X-ray tube 11, and the position of the compensation filter for the X-ray tube 11. In this situation, all the image acquisition conditions described above do not necessarily have to match completely between the first DSA image data and the second DSA image data. For example, when the pressure applied to the injector of the injected agent is substantially the same, the condition is such that the rising curve before reaching the expected injection speed will be substantially the same. Accordingly, it is sufficient when at least one selected from the pressure applied to the injector of the injected agent and the rising curve before reaching the expected injection speed is substantially the same. Further, for example, the above-mentioned conditions may include some differences as long as the parametric image data generating processes are not significantly impacted. That is to say, it is sufficient when at least one selected from among the abovementioned image acquisition conditions is substantially the same. In other words, the DSA image generating function 331 generates the first difference image data and the second difference image data by arranging at least one selected from among the following to be substantially the same between the first image acquisition conditions and the second image acquisition conditions: the injection conditions of the contrast agent, the X-ray radiation conditions, the size of the field of view radiated by the X-rays, the distance between the focal point of the X-ray tube that radiates the X-rays and the X-ray detector, the position of the couch on which the patient is placed, and the rotation center of the supporting machine that supports the X-ray tube and the detector.

As explained above, except that the image acquisition process is performed in the X-ray radiation direction changed at step S105, the DSA image generating function 331 performs the second-time image acquisition process by using substantially the same image acquisition conditions as the image acquisition conditions used for the first-time image acquisition process. In this situation, because the process performed by the DSA image generating function 331 in the second-time image acquisition process is basically the same as the DSA image generating process illustrated in FIG. 4, the explanation thereof will be omitted.

Subsequently, the parametric image generating function 332 performs a parametric image generating process (step S107). The parametric image generating process at step S107 is a process to generate the parametric image data from the second-time image acquisition process (which hereinafter may be referred to as the "second parametric image data").

In this situation, the parametric image generating function 332 performs the second-time parametric image generating process by using substantially the same processing conditions as the processing conditions used for the first-time parametric image generating process. That is to say, the parametric image generating function 332 generates the first parametric image data and the second parametric image data by using substantially the same processing conditions between the two, with respect to the method for identifying the inflow time and the color code defining the colors assigned in accordance with the temporal changes. In other words, the parametric image generating function 332 generates the first color image data and the second color image data by arranging at least one selected from the following to be substantially the same between the first processing conditions and the second processing conditions: the method for identifying the inflow time; and the color code defining the colors assigned in accordance with the temporal changes.

Further, when generating the parametric image data for a dynamic image, the parametric image generating function 332 generates the first parametric image data having a plurality of frames arranged in a temporal order and the second parametric image data having a plurality of frames arranged in a temporal order, by using substantially the same processing conditions between the two, with respect to the number of frames (the quantity of the frames) and the temporal change amount between the frames for the color code (a cyclic color code) used in the dynamic image. In this situation, all the processing conditions described above do not necessarily have to match completely between the first parametric image data and the second parametric image data. For example, the abovementioned processing conditions may include some differences as long as the parametric image data generating processes are not significantly impacted. That is to say, it is sufficient when at least one of the abovementioned processing conditions is substantially the same. In other words, when using a cyclic color code defining cyclic changes of the colors in response to the changes in the inflow time, the parametric image generating function 332 generates the first color image data having the plurality of frames arranged in a temporal order and the second color image data having the plurality of frames arranged in a temporal order, by arranging at least one selected from the following to be substantially the same between the first processing conditions and the second processing conditions: the number of frames (the quantity of the frames); and the temporal change amount between the frames used by the cyclic color code.

As explained above, the parametric image generating function 332 performs the second-time parametric image generating process by using substantially the same processing conditions as the processing conditions used for the first-time parametric image generating process. The process performed by the parametric image generating function 332 during the second-time parametric image generating process is basically the same as the parametric image generating process illustrated in FIG. 5. However, when the same color codes are used, the process of generating the color codes (step S302) does not have to be performed. Further, because the process of identifying the inflow time (step S301) and the process of generating the parametric image data (step S303) are the same, the explanation thereof will be omitted.

After that, the display controlling function 333 causes a stereoscopic image to be displayed on the basis of the two pieces of parametric image data having mutually-different viewpoints (step S108). For example, the display controlling function 333 causes the stereoscopic image to be displayed on the basis of the first parametric image data generated at step S104 and the second parametric image data generated at step S107.

For example, when the X-ray radiation position in the first-time image acquisition process is (LAO 90, CRA/CAU 0), whereas the X-ray radiation position in the second-time image acquisition process is (LAO 95, CRA/CAU 0), the display controlling function 333 realizes a stereoscopic display by using the first parametric image data as data for the left eye and the second parametric image data as data for the right eye. More specifically, the display controlling function 333 realizes the stereoscopic display by causing the first parametric image data and the second parametric image data to be displayed by either a display device that enables the viewer to view a stereoscopic image without wearing eyeglasses or a display device that operates in synchronization with eyeglasses dedicated for stereoscopic viewing. As the display device realizing the stereoscopic display, any conventional stereoscopic display device may be used.

More specifically, the display controlling function 333 causes a stereoscopic image representing a still image to be displayed, on the basis of the first parametric image data representing a still image and the second parametric image data representing a still image. Alternatively, the display controlling function 333 causes a stereoscopic image representing a dynamic image to be displayed in the manner of a synchronization display, on the basis of the first parametric image data representing a dynamic image and the second parametric image data representing a dynamic image.

FIG. 10 is a drawing for explaining a synchronization display realized by the display controlling function 333 according to the first embodiment. FIG. 10 illustrates the order of frame numbers of the frames that become subject to the synchronization display, as the playback time elapses.

As illustrated in FIG. 10, when causing a stereoscopic image representing a dynamic image to be displayed, the display controlling function 333 causes stereoscopic images to be displayed in the temporal order, on the basis of the first parametric image data and the second parametric image data representing frames that are in mutually-the-same temporal phase. More specifically, the display controlling function 333 causes a stereoscopic image in the first frame to be displayed on the basis of the first parametric image data of the first frame and the second parametric image data of the first frame. Further, the display controlling function 333 causes a stereoscopic image in the second frame to be displayed on the basis of the first parametric image data of the second frame and the second parametric image data of the second frame. In this manner, the display controlling function 333 causes a stereoscopic image in the N-th frame to be displayed on the basis of the first parametric image data of the N-th frame and the second parametric image data of the N-th frame.

As explained above, the display controlling function 333 causes the stereoscopic image to be displayed on the basis of the two pieces of parametric image data having the mutually-different viewpoints. With this arrangement, the X-ray diagnosis apparatus 1 is able to provide the image that enables the viewer to have a stereoscopic view in the parametric imaging process.

After that, the processing circuitry 33 performs a correcting process (step S109). For example, the processing circuitry 33 performs an arbitrary correcting process in response to a request from the operator, the correcting process being selected from among the following: a correcting process to re-generate parametric image data; a correcting process to align the inflow times in mutually-the-same position; and a correcting process to correct frame numbers in a non-synchronization display mode. Each of these correcting processes will be explained below.

The Correcting Process to Re-generate Parametric Image Data

The correcting process to re-generate parametric image data is a correcting process that is performed when an instruction indicating that the processing conditions for the parametric image generating process be changed is received. For example, when having received an instruction indicating that the processing conditions for the parametric image generating process be changed, the parametric image generating function 332 re-generates first parametric image data and second parametric image data by using processing conditions after the change.

For example, when having received an instruction from the operator indicating that the cycle of the color code, which is one of the processing conditions, should be changed from "T" to "T/2", the parametric image generating function 332 re-generates a color code by using the post-change cycle "T/2" of the color code. Further, the parametric image generating function 332 re-generates first parametric image data and second parametric image data by using the re-generated color code.

As explained above, the parametric image generating function 332 performs the correcting process to re-generate the parametric image data. In other words, when having received an instruction indicating that one selected from the first processing conditions and the second processing conditions should be changed, the parametric image generating function 332 re-generates the first color image data and the second color image data by using the processing condition after the change.

The Correcting Process to Align the Inflow Times in Mutually-the-same Position

The correcting process to align the inflow times in mutually-the-same position is a correcting process performed by identifying mutually-the-same position within two pieces of parametric image data having mutually-different viewpoints. For example, when having received an instruction from the operator indicating that a correcting process should be performed to align the inflow times in mutually-the-same position, the parametric image generating function 332 identifies mutually-the-same position within the first parametric image data and the second parametric image data.

For example, by using an anatomical characteristic within the two pieces of parametric image data, the parametric image generating function 332 determines positions (pixels) in the first parametric image data into correspondence with positions (pixels) in the second parametric image data. Further, the parametric image generating function 332 performs the correcting process to align the inflow times by comparing the inflow times in mutually-the-same position with each other.

More specifically, the parametric image generating function 332 selects a representative region (e.g., pixels indicating branching of a blood vessel) from the first parametric image data. Further, the parametric image generating function 332 identifies such a region in the second parametric image data that has substantially the same anatomical structure as that in the representative region within the first parametric image data. With respect to the identified region, the parametric image generating function 332 further calculates the difference between the inflow time in the first-time image acquisition process and the inflow time in the second-time image acquisition process. After that, the parametric image generating function 332 corrects the inflow times of all the pixels from either the first-time image acquisition process or the second-time image acquisition process so as to eliminate the calculated difference. Further, the parametric image generating function 332 re-generates one of the two pieces of parametric image data of which the inflow times have been corrected, by using the corrected inflow times.

As explained above, the parametric image generating function 332 performs the correction process to align the inflow times calculated from mutually-the-same position between the first DSA image data and the second DSA image data. After that, the parametric image generating function 332 re-generates at least one selected from the first parametric image data and the second parametric image data.

The explanation above merely describes an example, and possible embodiments are not limited to the example described above. For instance, the explanation above describes the example in which the single representative region is selected. However, possible embodiments are not limited to this example. For instance, two or more representative regions may be selected. In that situation, it is desirable to configure the parametric image generating function 332 so as to calculate the difference by using an average value of inflow times among the plurality of regions.

Further, for example, the explanation above describes the example in which the difference is calculated by using the inflow times in mutually-the-same region. However, possible embodiments are not limited to this example. For instance, the parametric image generating function 332 may calculate a difference by using time-concentration profile in mutually-the-same region.

Further, for example, the explanation above describes the example in which the correcting process to align the inflow times in the mutually-the-same position is performed in response to the instruction received from the operator. However, possible embodiments are not limited to this example. For instance, the parametric image generating function 332 may automatically perform this correcting process without receiving any instruction from the operator. When this correcting process is automatically performed, the correcting process may be performed before the process of displaying the stereoscopic image (step S108) is performed.

The Correcting Process to Correct the Frame Numbers in the Non-synchronization Display Mode The correcting process to correct the frame numbers in the non-synchronization display mode is a correcting process performed in the non-synchronization display mode, when the parametric image data is generated as a dynamic image (the CCC method).

For example, when having received a request to use the non-synchronization display mode, the display controlling function 333 changes the temporal phases of the frames to be displayed in a temporal order with respect to one selected from the first parametric image data having a plurality of frames and the second parametric image data having a plurality of frames.

FIG. 11 is a drawing for explaining the frame number correcting process in the non-synchronization display mode according to the first embodiment. FIG. 11 illustrates an example in which the operator requested the non-synchronization display mode during the synchronization display illustrated in FIG. 10.

As illustrated in FIG. 11, when having received a request to use the non-synchronization display mode from the operator, the display controlling function 333 cancels the synchronization display of the first parametric image data and the second parametric image data. In this situation, when the operator instructs that the frame numbers of one of the two pieces of parametric image data should be changed, the display controlling function 333 changes the frame numbers in the designated one of the two pieces of parametric image data. For example, when the first parametric image data of the first frame and the second parametric image data of the first frame are to be displayed, the display controlling function 333 receives an instruction from the operator indicating that the frame numbers in the second parametric image data should each be incremented. In that situation, in response to the received instruction, the display controlling function 333 performs the correcting process to increment each of the frame numbers in the second parametric image data. In other words, the display controlling function 333 causes a stereoscopic image in the first frame to be displayed on the basis of the first parametric image data of the first frame and the second parametric image data of the second frame. When the operator instructs that the non-synchronization display mode should be ended, the display controlling function 333 ends the non-synchronization display mode and returns to the synchronization display mode.

As explained above, when having received the request to use the non-synchronization display mode, the display controlling function 333 changes the temporal phases (the frame numbers) of the frames displayed in the temporal order, with respect to one selected from the first parametric image data having the plurality of frames and the second parametric image data having the plurality of frames.

As explained above, the processing circuitry 33 performs any of the correcting processes. After that, for example, when having received an instruction from the operator indicating that the image acquisition process should be ended, the processing circuitry 33 ends the process illustrated in FIG. 3.

The processing procedure illustrated in FIG. 3 described above is merely an example. Possible embodiments are not limited to the example illustrated in FIG. 3. For instance, the processing procedure illustrated in FIG. 3 does not necessarily have to be performed in the order described above. For example, the correcting process (step S109) does not necessarily have to be performed. For example, the correcting process may be executed by the operator as necessary. Further, for example, when the correcting process to align the inflow times in the mutually-the-same position (step S109) is automatically performed, it is also acceptable to perform the correcting process before the process of displaying the stereoscopic image (step S108) is performed. Further, although the correcting process was explained above as a process of changing the temporal phases in units of frames, it is also acceptable to change the time in smaller units than the frames. More specifically, the time may be changed in units each corresponding to $\Delta t/5$. In that situation, because there is no second parametric image data corresponding to a time shift of $\Delta t/5$, it will be necessary to generate parametric image data again.

Further, with reference to FIG. 3, the example is explained in which the X-ray parametric imaging-purpose image acquisition program is used as a dedicated image acquisition program. However, possible embodiments are not limited to this example. For instance, the second-time image acquisition process may be performed by using substantially the same image acquisition conditions, by using a conventional DSA image acquisition program. In that situation, two pieces of parametric image data having mutually-different parallaxes are generated by applying the conventional parametric imaging-purpose program to two pieces of DSA image data that are taken, by using substantially the same processing conditions.

As explained above, the X-ray diagnosis apparatus 1 according to the first embodiment is configured to generate the two pieces of DSA image data having the mutually-different viewpoints, in the time series, by using substantially the same image acquisition conditions between the two. Further, the X-ray diagnosis apparatus 1 is configured to generate the two pieces of parametric image data having the mutually-different viewpoints from the generated two pieces of DSA image data, by using substantially the same processing conditions between the two. Further, the X-ray diagnosis apparatus 1 is configured to cause the stereoscopic image to be displayed on the basis of the generated two pieces of parametric image data. With this arrangement, the X-ray diagnosis apparatus 1 is able to provide the image that enables the viewer to have a stereoscopic view in the parametric imaging process.

Incidentally, there is a problem that, during the stereoscopic display process, the viewer is not able to have a stereoscopic view unless mutually-the-same position in the left and the right images is rendered in mutually-the-same color. Further, during the parametric imaging process, because the images are expressed on the basis of the temporal changes in the concentration level of the contrast agent, it is required to achieve a frame rate with which the viewer is able to view the temporal changes. In other words, to provide images that enable the viewer to have a stereoscopic view in a parametric imaging process, it is required to generate parallax images in which mutually-the-same position is rendered in mutually-the-same color, while maintaining a frame rate equal to or higher than a certain level. To cope with this situation, the X-ray diagnosis apparatus 1 according to the first embodiment generates the parallax images (the parametric image data) in which mutually-the-same position is rendered in mutually-the-same color, while maintaining a frame rate equal to or higher than a certain level, by performing the process described below.

Figure 12:
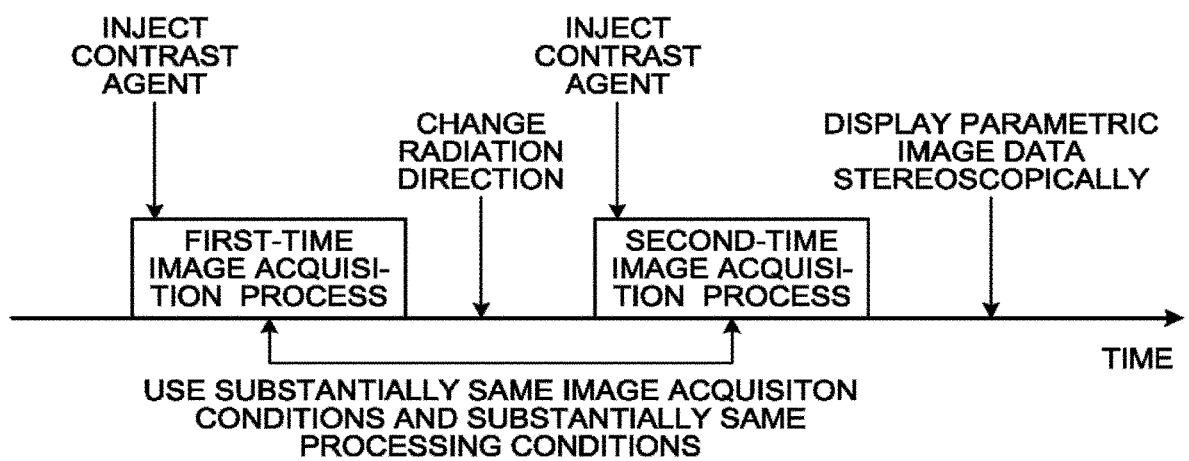
FIG. 12 is a drawing for explaining advantageous effects of the X-ray diagnosis apparatus according to the first embodiment.

FIG. 12 is a drawing for explaining advantageous effects of the X-ray diagnosis apparatus 1 according to the first embodiment. As illustrated in FIG. 12, for example, the X-ray diagnosis apparatus 1 according to the first embodiment performs an image acquisition process twice to take pieces of parametric image data for the left and for the right, to realize a stereoscopic display. In other words, the X-ray diagnosis apparatus 1 takes two pieces of DSA image data having mutually-different viewpoints by performing the first-time image acquisition process and subsequently changing the X-ray radiation direction, before performing the second-time image acquisition process. After that, the X-ray diagnosis apparatus 1 generates the two pieces of parametric image data having mutually-different viewpoints by calculating the inflow times of the contrast agent in the two pieces of DSA image data that were taken and assigning the colors corresponding to the calculated inflow times.

In this situation, during the image acquisition process performed twice, the X-ray diagnosis apparatus 1 according to the first embodiment takes a plurality of frames of the DSA image data in the time series, while the radiation direction is fixed to each of the radiation directions. With this arrangement, the X-ray diagnosis apparatus 1 is able to maintain the frame rate of each of the pieces of DSA image data corresponding to a different one of the radiation directions, so as to be equal to or higher than a certain level.

Further, during the image acquisition process performed twice, the X-ray diagnosis apparatus 1 according to the first embodiment acquires the two pieces of DSA image data by using substantially the same image acquisition conditions between the two and further generates the two pieces of parametric image data by using substantially the same processing conditions between the two, except that the X-ray radiation directions (the radiation positions of the X-ray tube 11) are different between the two. For example, the X-ray diagnosis apparatus 1 acquires the two pieces of DSA image data having the mutually-different viewpoints by arranging the following conditions to be substantially the same between the two: the radiation conditions other than the X-ray radiation directions; the injection conditions used for injecting the contrast agent; and the image acquisition conditions such as the size of the field of view, the SID, the position of the couch 14, and the Iso-Center. Further, for example, the X-ray diagnosis apparatus 1 generates the two pieces of parametric image data having the mutually-different viewpoints by arranging the processing conditions such as the method for identifying the inflow times and/or the color code (or the cyclic color codes for a dynamic image), to be substantially the same between the two. With these arrangements, the X-ray diagnosis apparatus 1 is able to generate the two pieces of parametric image data in which mutually-the-same position is rendered in mutually-the-same color.

As explained above, the X-ray diagnosis apparatus 1 according to the first embodiment generates the two pieces of parametric image data in which mutually-the-same position is rendered in mutually-the-same color, while maintaining the frame rate to be equal to or higher than a certain level. Consequently, the X-ray diagnosis apparatus 1 is able to provide the images that enable the viewer to have a stereoscopic view in the parametric imaging process.

Further, for example, when having received the instruction indicating that the processing conditions of the parametric image generating process be changed, the X-ray diagnosis apparatus 1 according to the first embodiment performs the correcting process to re-generate the two pieces of parametric image data having the mutually-different viewpoints. With this arrangement, for example, even when the operator has changed the processing conditions of the parametric image generating process, the X-ray diagnosis apparatus 1 is able to generate/display two pieces of parametric image data having mutually-different viewpoints, by using processing conditions that are the same between the two, at all times.

Further, for example, the X-ray diagnosis apparatus 1 according to the first embodiment performs the correcting process to align the inflow times calculated from mutually-the-same position in the first DSA image data and the second DSA image data. After that, the parametric image generating function 332 re-generates at least one selected from the first parametric image data and the second parametric image data. Accordingly, for example, when a difference has occurred between inflow times in mutually-the-same position, the X-ray diagnosis apparatus 1 is able to correct the difference.

Further, for example, when having received the request to use the non-synchronization display mode while displaying a dynamic image, the X-ray diagnosis apparatus 1 according to the first embodiment changes the temporal phases (either the frame numbers or frame times) of the frames displayed in the temporal order, with respect to one selected from the first parametric image data having the plurality of frames and the second parametric image data having the plurality of frames. With this arrangement, the X-ray diagnosis apparatus 1 is able to change the temporal phases of the frames in the parametric image data, in units of time periods of steps used by the color codes for the parametric image data representing the dynamic image, or in units smaller than those time periods. For example, because the color codes change rapidly during a dynamic image display process, even a small difference in the inflow times may make it impossible to render mutually-the-same position in mutually-the-same color, in some situations. As a specific example, when a medical doctor has moved the position of a catheter inserted in the patient P between the first-time image acquisition process and the second-time image acquisition process, a difference occurs in the inflow times. In that situation, the X-ray diagnosis apparatus 1 changes the temporal phases of the frames in units of time periods of the steps ($\Delta T$) used by the color codes or in units smaller than those time periods. The X-ray diagnosis apparatus 1 is therefore able to adjust the colors in the parametric image data with an extremely fine pitch.

Modification Examples of the First Embodiment

The viewing direction described in the first embodiment may automatically be determined in accordance with the extending direction of the blood vessel.

For example, for each of various sites, the X-ray diagnosis apparatus 1 has stored therein information about the extending direction of a major blood vessel. For example, with respect to the "brain", the X-ray diagnosis apparatus 1 has information indicating the "patient's head/toe direction" stored in a storage device.

Further, the processing circuitry 33 receives an instruction from the operator designating an image acquisition region. After that, the processing circuitry 33 refers to the information about the extending direction of the major blood vessel at each of the regions and obtains the information about the extending direction of the major blood vessel corresponding to the designated image acquisition region. For example, when the "brain" is designated as the interested region, the processing circuitry 33 obtains the information indicating the "patient's head/toe direction" from the storage device. Further, the processing circuitry 33 determines the viewing direction on the basis of the obtained information about the extending direction of the blood vessel. In this situation, the processing circuitry 33 determines the viewing direction so as to be orthogonal to the extending direction of the blood vessel. For example, when the extending direction of the blood vessel is the "patient's head/toe direction", the processing circuitry 33 determines the "patient's left/right direction" as the viewing direction. After that, the processing circuitry 33 performs an image acquisition process by using the determined viewing direction. The present example is explained while the extending directions of the blood vessels are limited to the "patient's head/toe direction" and the "patient's left/right direction" for the purpose of keeping the explanation simple. However, the extending directions of blood vessels are not limited to these two directions. For example, there are blood vessels extending so as to be inclined at an angle of 45 degrees from the X-axis direction toward the Z-axis direction and blood vessels extending so as to be further inclined at an angle of 45 degrees toward the Y-axis direction. In those situations, for the purpose of having a stereoscopic view of the blood vessel of interest, it is most desirable to change the viewing direction within a plane perpendicular to the extending direction thereof. Accordingly, it is also acceptable to identify the extending direction of the blood vessel from a 3D CT image, for example, so as to determine the viewing direction on the basis of the identified angle. Alternatively, when it is sufficient to approximately find out a stereoscopic positional relationship, changing the viewing angle to either the "patient's left/right direction" or the "patient's head/toe direction" makes it possible to recognize the stereoscopic structure to some extent. This method is advantageous because it is possible to eliminate the need to designate an angle in a complicated manner and because it is possible to simply choose from the two options of the "patient's left/right direction" and the "patient's head/toe direction", for example.

By using this configuration, the X-ray diagnosis apparatus 1 is able to determine the viewing direction corresponding to the extending direction of the major blood vessel at each region, without the operator having to designate a viewing direction in consideration of the extending direction of the blood vessel. The configuration described above is merely an example, and possible embodiments are not limited to this example. For instance, the information about the extending direction of the blood vessel may be stored for each of different types of blood vessels. In that situation, when the operator designates a blood vessel subject to an image acquisition process, the processing circuitry 33 determines a viewing direction corresponding to the type of the blood vessel. Alternatively, it is also acceptable to store viewing directions corresponding to the extending directions of the blood vessels, instead of storing the extending directions of the blood vessels. In that situation, when the operator designates an image acquisition region (or a blood vessel), the processing circuitry 33 is able to read a viewing direction corresponding to the type of the blood vessel from the storage device.

Second Embodiment

In the first embodiment, the example is explained in which the X-ray tube 11 having a single focal point is used; however, possible embodiments are not limited to this example. For instance, as the X-ray tube 11, a stereoscopic X-ray tube having two focal points may be used. The stereoscopic X-ray tube is an X-ray tube configured to radiate X-rays while switching between the two focal points.

In other words, the DSA image generating function 331 according to a second embodiment is configured to generate first DSA image data and second DSA image data in mutually-the-same time period, by using the stereoscopic X-ray tube. Further, the parametric image generating function 332 is configured to generate first parametric image data and second parametric image data after correcting a time difference caused by the switching between the two focal points.

Figure 13:
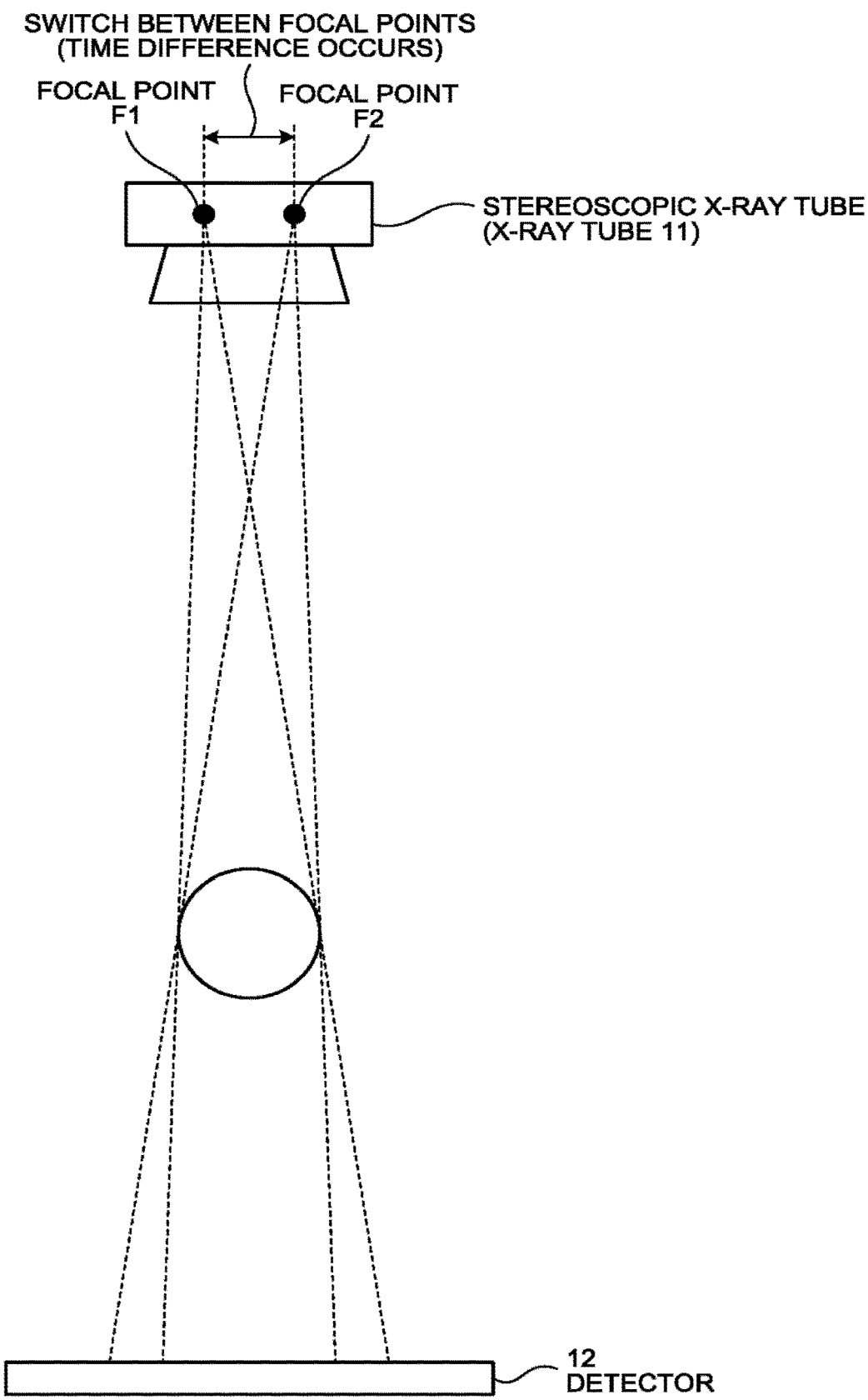
FIG. 13 is a drawing for explaining an image acquisition process using a stereoscopic X-ray tube according to a second embodiment.

FIG. 13 is a drawing for explaining an image acquisition process using the stereoscopic X-ray tube according to the second embodiment. FIG. 13 illustrates an example in which an image acquisition process is performed by using the stereoscopic X-ray tube having a focal point F1 and a focal point F2.

As illustrated in FIG. 13, when having received pressing of the X-ray trigger button, the DSA image generating function 331 generates DSA image data having a plurality of frames arranged in a time series, while switching between the focal point F1 and the focal point F2. That is to say, when a contrast agent is injected one time, the DSA image generating function 331 takes the first DSA image data having the plurality of frames and the second DSA image data having the plurality of frames. In other words, the DSA image generating function 331 acquires the first DSA image data having the plurality of frames and the second DSA image data having the plurality of frames, in the situation where the contrast agent injection conditions and the X-ray radiation conditions are the same between the two. The process performed by the DSA image generating function 331 according to the second embodiment is the same as the process explained in the first embodiment, except that the two pieces of DSA image data having a parallax are generated with the injection of the contrast agent performed once. Accordingly, the explanation thereof will be omitted.

In this situation, because of the switching between the focal point F1 and the focal point F2, the pieces of DSA image data taken by using the different focal points will have a time difference. For example, when the image acquisition process is performed while switching between the focal points in the order of "the focal point F1→the focal point F2→the focal point F1→the focal point F2→ . . . ", the image acquisition time of each of the frames taken by using the focal point F2 is later than the image acquisition time of each of the frames taken by using the focal point F1 by a length corresponding to the time difference (e.g., 0.1 seconds).

To cope with this situation, the parametric image generating function 332 generates the first parametric image data and the second parametric image data after correcting the time difference caused by the switching between the focal points. For example, when the image acquisition process is performed by switching between the focal points in the order of "the focal point F1→the focal point F2→the focal point F1→the focal point F2→ . . . ", a pair of images taken by using the focal point F1 and the focal point F2 is recorded as images in the first frame. In this situation, the images recorded as the pair have recorded with mutually-the-same image acquisition time. For example, when the image acquisition time of the image in the first frame acquired by using the focal point F1 is assumed to be 0 seconds, while the time difference from the time when the image using the focal point F1 is acquired to the time when the image using the focal point F2 is acquired is assumed to be 0.1 seconds, the image acquisition time of the image acquired by using the focal point F2 is 0.1 seconds. However, at the time of the recording, because the image using the focal point F1 and the image using the focal point F2 are recorded as the pair of images, only one image acquisition time is recorded. As a result, the image acquisition time of the image using the focal point F2 is different from the actual image acquisition time. To cope with this situation, the parametric image generating function 332 adds the time difference (0.1 seconds in the present example) from the time when the image using the focal point F1 is acquired to the time when the image using the focal point F2 is acquired, to each of the image acquisition times of the frames acquired by using the focal point F2. In this manner, the parametric image generating function 332 corrects the time difference between the image acquisition time of each of the frames taken by using the focal point F1 and the image acquisition time of each of the frames taken by using the focal point F2. After that, the parametric image generating function 332 generates pieces of parametric image data by using pieces of DSA image data in which the time differences in the image acquisition time among the frames have been corrected. The process performed by the parametric image generating function 332 according to the second embodiment is the same as the process described in the first embodiment, except that the time difference from the time when the image using the focal point F1 is acquired to the time when the image using the focal point F2 is acquired is corrected. Accordingly, the explanation thereof will be omitted.

As explained above, even when using the stereoscopic X-ray tube having the two focal points, the X-ray diagnosis apparatus 1 is able to provide an image that enables the viewer to have a stereoscopic view in the parametric imaging process.

The explanation above merely describes an example, and possible embodiments are not limited this example. For instance, although the above description explains the example in which the stereoscopic X-ray tube is used, possible embodiments are not limited to this example. It is also acceptable to use a flying focus method by which the position of a focal point can be switched by an electromagnetic deflection. In other words, the second embodiment is applicable to situations where an X-ray tube configured to radiate X-rays while switching between two focal points is used.

Third Embodiment

In the embodiments described above, the example is explained in which the region of interest substantially coincides with the rotation center (the Iso-Center) of the C-arm 13; however, possible embodiments are not limited to this example. For instance, it is also possible to increase a magnification ratio of an X-ray optical system by bringing the region of interest closer to the X-ray tube 11.

Figure 14:
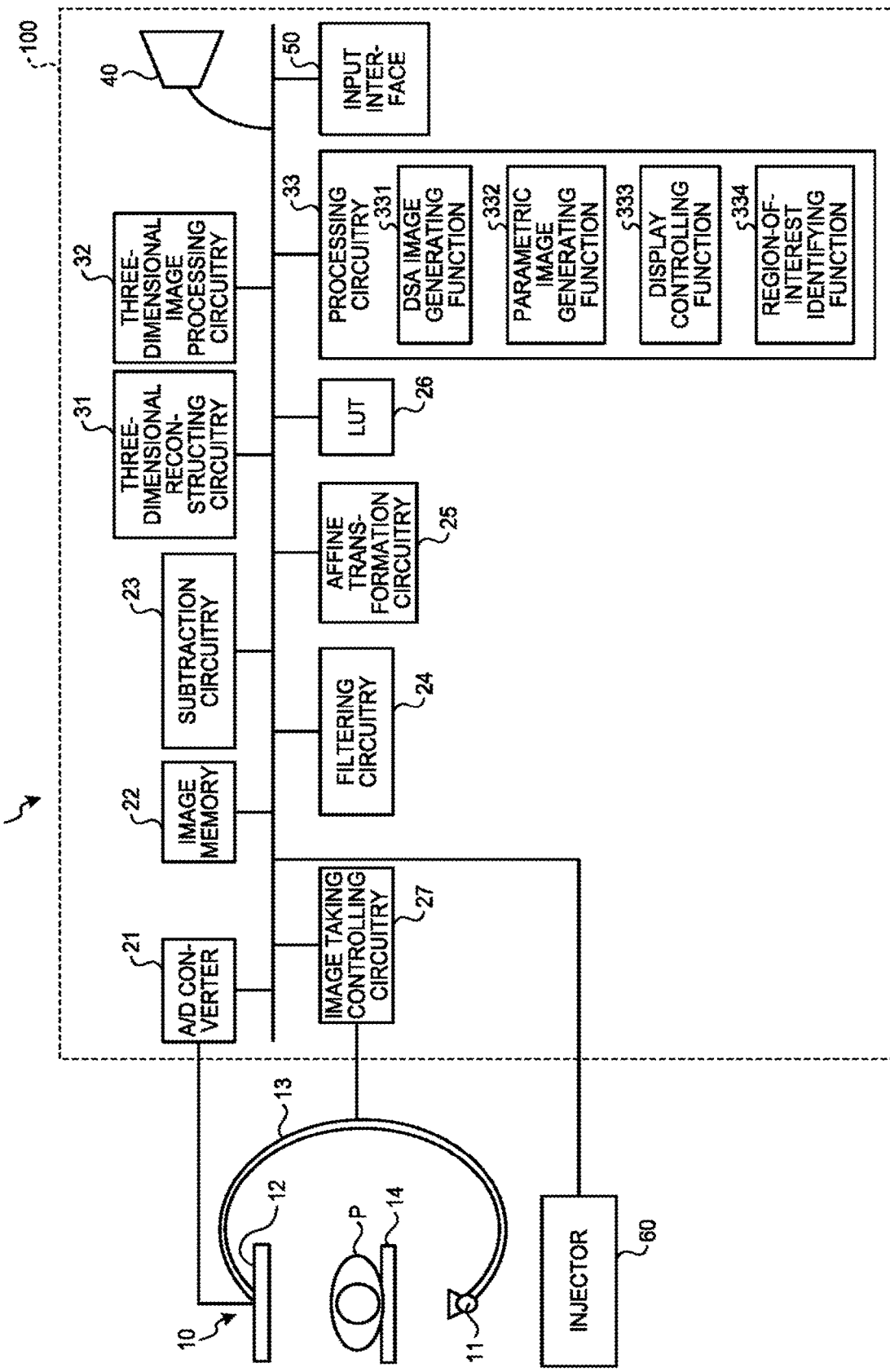
FIG. 14 is a drawing illustrating an exemplary configuration of an X-ray diagnosis apparatus according to a third embodiment.

FIG. 14 is a drawing illustrating an exemplary configuration of the X-ray diagnosis apparatus 1 according to a third embodiment. The X-ray diagnosis apparatus 1 according to the third embodiment has a configuration similar to that of the X-ray diagnosis apparatus 1 illustrated in FIG. 1 and is different in that the processing circuitry 33 further includes a region-of-interest identifying function 334. Accordingly, the third embodiment will be explained while a focus is placed on the difference from the first embodiment. Some of the elements having the same functions as those explained in the first embodiment will be referred to by using the same reference characters as those in FIG. 1, and the explanation thereof will be omitted.

The region-of-interest identifying function 334 is configured, when having received an operation to designate a region of interest, to identify the position of the region of interest with respect to an image acquisition system device and to control the image acquisition system device so as to take an image of the identified position of the region of interest. The image acquisition system device includes, for example, the X-ray tube 11, the detector 12, and the C-arm 13.

Figure 15:
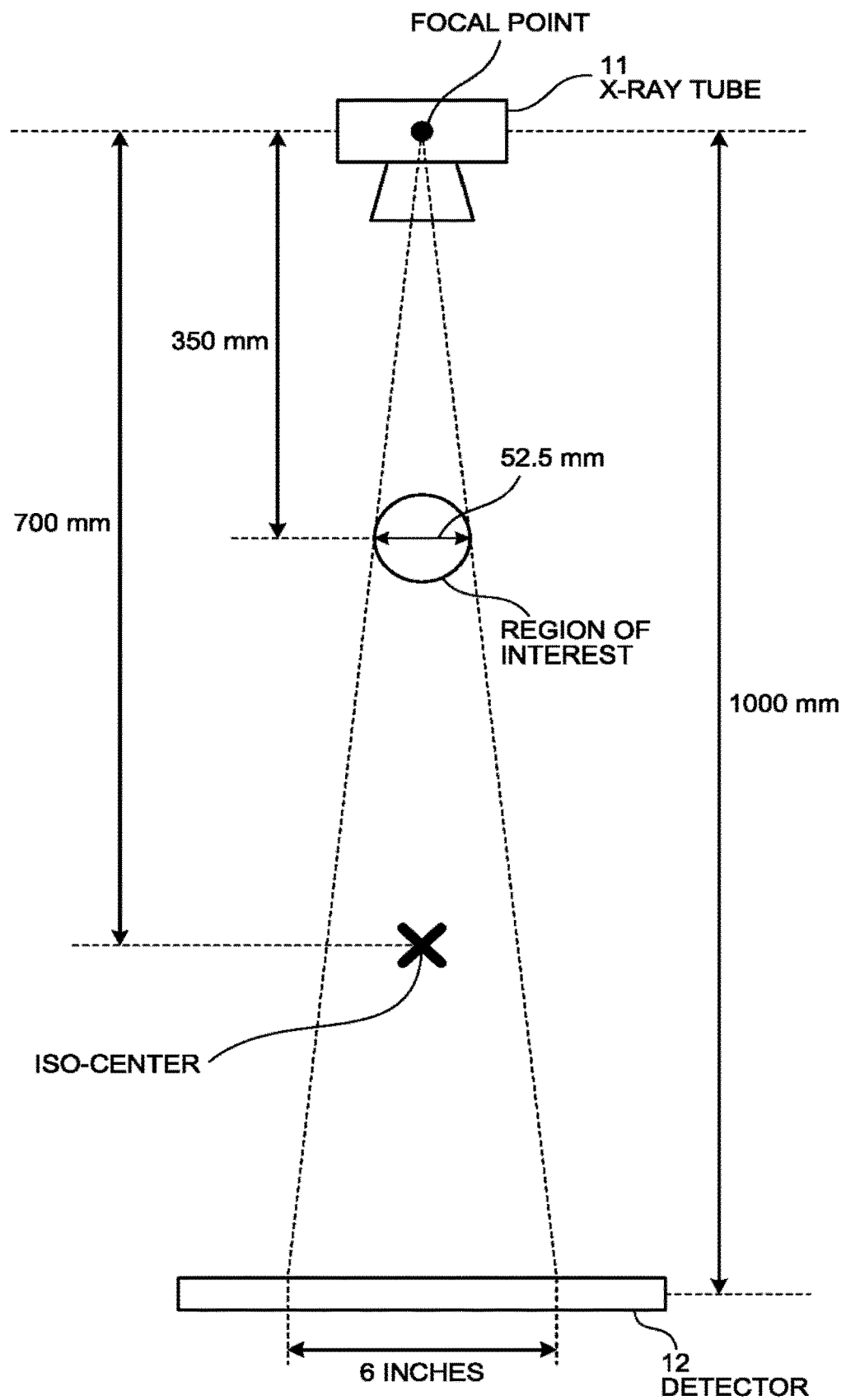
FIG. 15 is a drawing for explaining a process performed by a region-of-interest identifying function according to the third embodiment.

FIGS. 15 to 19 are drawings for explaining a process performed by the region-of-interest identifying function 334 according to the third embodiment. FIGS. 15 to 19 illustrate transitions in the positional relationship between a region of interest and an image acquisition system device in the example where the magnification ratio of an X-ray optical system is increased. FIG. 15 illustrates an example in which the SID is 1,000 [mm], while the FOV is 6 [inches], and the distance from the focal point of the X-ray tube 11 to the Iso-Center is 700 [mm]. When the magnification ratio of the X-ray optical system is increased, it is desirable to use the smallest size of the focal point for the purpose of preventing X-ray images from becoming out of focus.

As illustrated in FIG. 15, for example, when having received an operation from the operator designating a region of interest in two X-ray fluoroscopic images having mutually-different viewpoints, the region-of-interest identifying function 334 determines a magnification ratio used in the X-ray optical system. More specifically, when having received the operation of designating the center point of the region of interest and the area of the region of interest within the X-ray fluoroscopic images, the region-of-interest identifying function 334 determines the magnification ratio used by the X-ray optical system so that it is possible to take an image of the received area of the region of interest by using an FOV that was set in advance. For example, when the dimension of the region of interest designated by the operator is 52.5 [mm], the region-of-interest identifying function 334 calculates the magnification ratio used by the X-ray optical system to be 2.86 times, because the SID is 1,000 [mm] while the FOV is 6 [inches]. In that situation, because the distance from the focal point of the X-ray tube 11 to the center of the region of interest is 350 [mm], the image acquisition process is performed with an extremely higher magnification ratio compared to the distance (700 [mm]) from the focal point of the X-ray tube 11 to the Iso-Center.

Further, the region-of-interest identifying function 334 identifies the center position of the region of interest within a three-dimensional space (the real space) on the basis of the center point of the region of interest designated in the X-ray fluoroscopic images. In other words, the region-of-interest identifying function 334 identifies the positional relationship between the region of interest and the image acquisition system device within the three-dimensional space.

Figure 16:
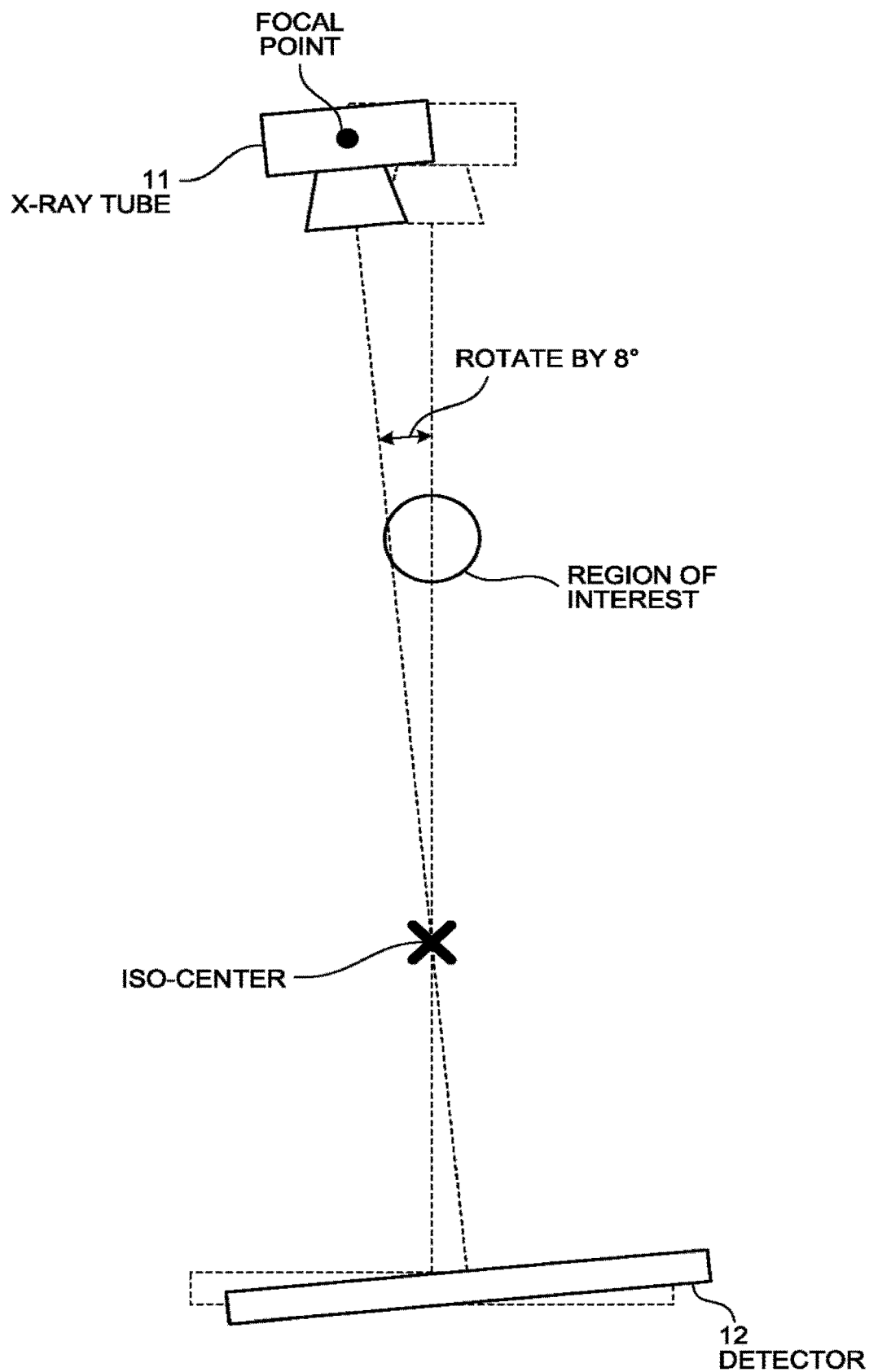
FIG. 16 is another drawing for explaining the process performed by the region-of-interest identifying function according to the third embodiment.

Subsequently, as illustrated in FIG. 16, when the C-arm 13 is rotated while being centered on the Iso-Center with a parallax angle of 8 degrees, the position of the region of interest projected on the detector (FPD) 12 shifts. Accordingly, the region-of-interest identifying function 334 identifies the amount of the shift (the shift amount) and controls the image acquisition system device in accordance with the identified shift amount. In FIG. 16, the positions of the X-ray tube 11 and the detector 12 after the rotation are indicated with the solid lines, while the positions of the X-ray tube 11 and the detector 12 before the rotation are indicated with the broken lines.

Figure 17:
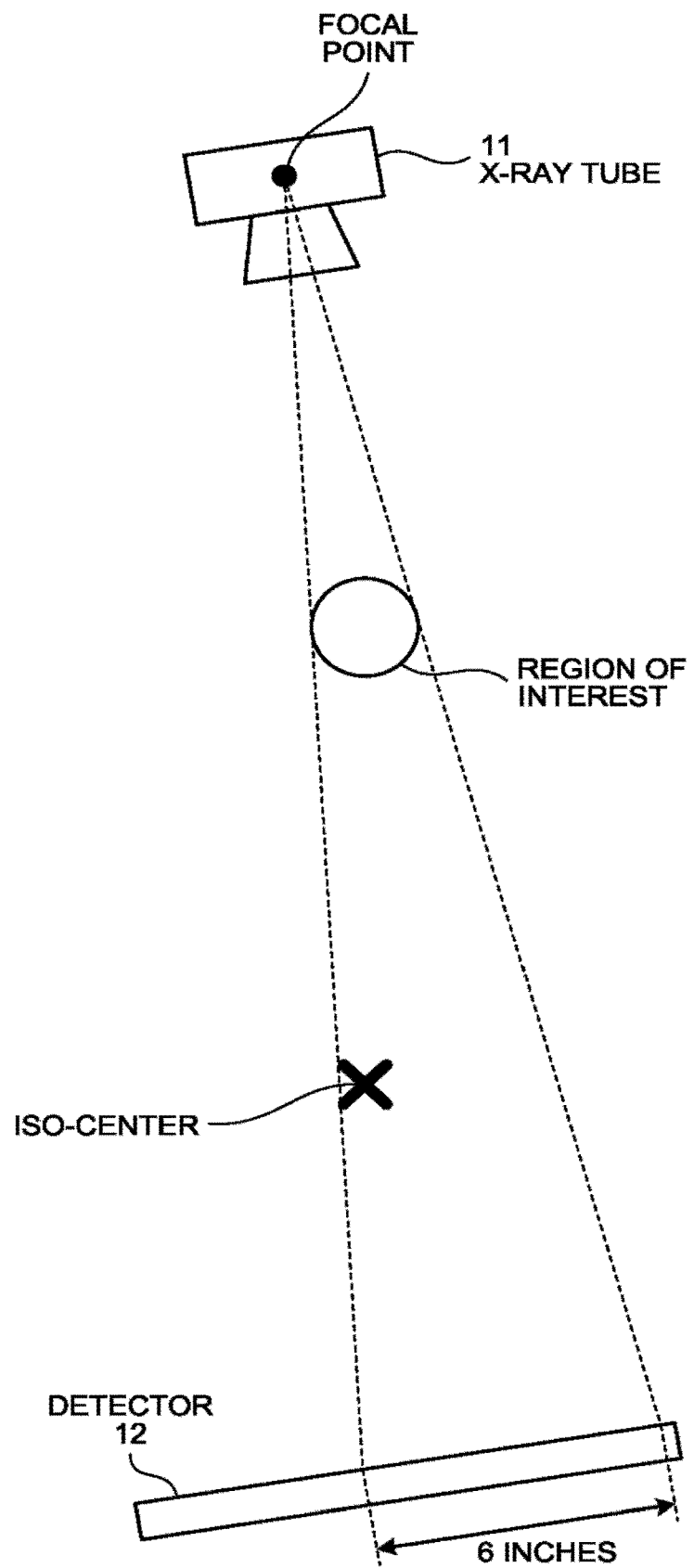
FIG. 17 is yet another drawing for explaining the process performed by the region-of-interest identifying function according to the third embodiment.
Figure 18:
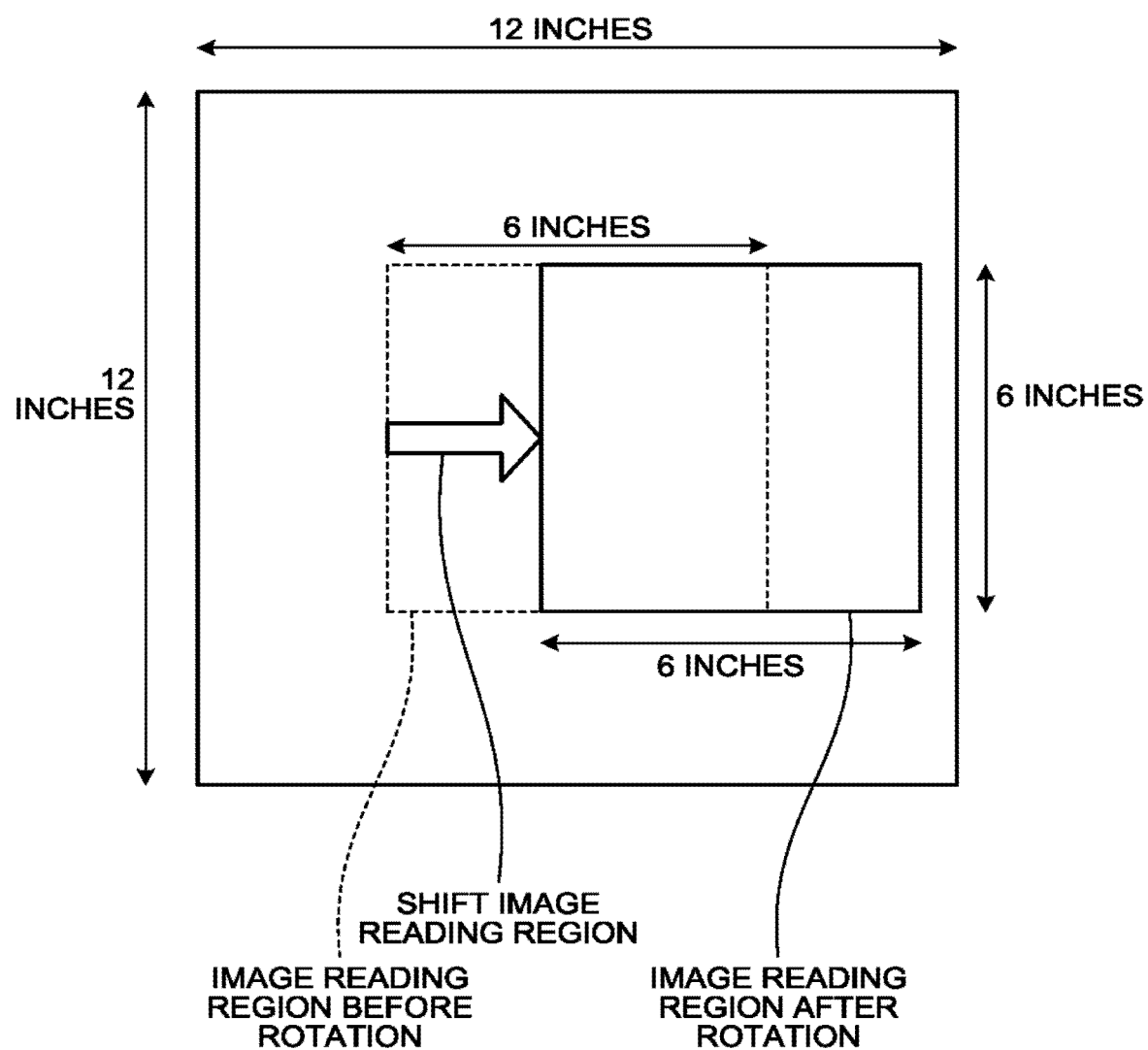
FIG. 18 is yet another drawing for explaining the process performed by the region-of-interest identifying function according to the third embodiment.

For example, as illustrated in FIGS. 17 and 18, when the shifted region-of-interest is included in the area of the detector 12, the region-of-interest identifying function 334 shifts an image reading region of the detector 12. For example, when the dimension of the detector 12 is 12 [inches], the region-of-interest identifying function 334 controls the image acquisition system device so as to shift the 6-inch image reading region by 69.9268 [mm]. In FIG. 18, the position of the image reading region after the rotation (the shift) is indicated with the solid line, whereas the position of the image reading region before the rotation is indicated with the broken line.

Figure 19:
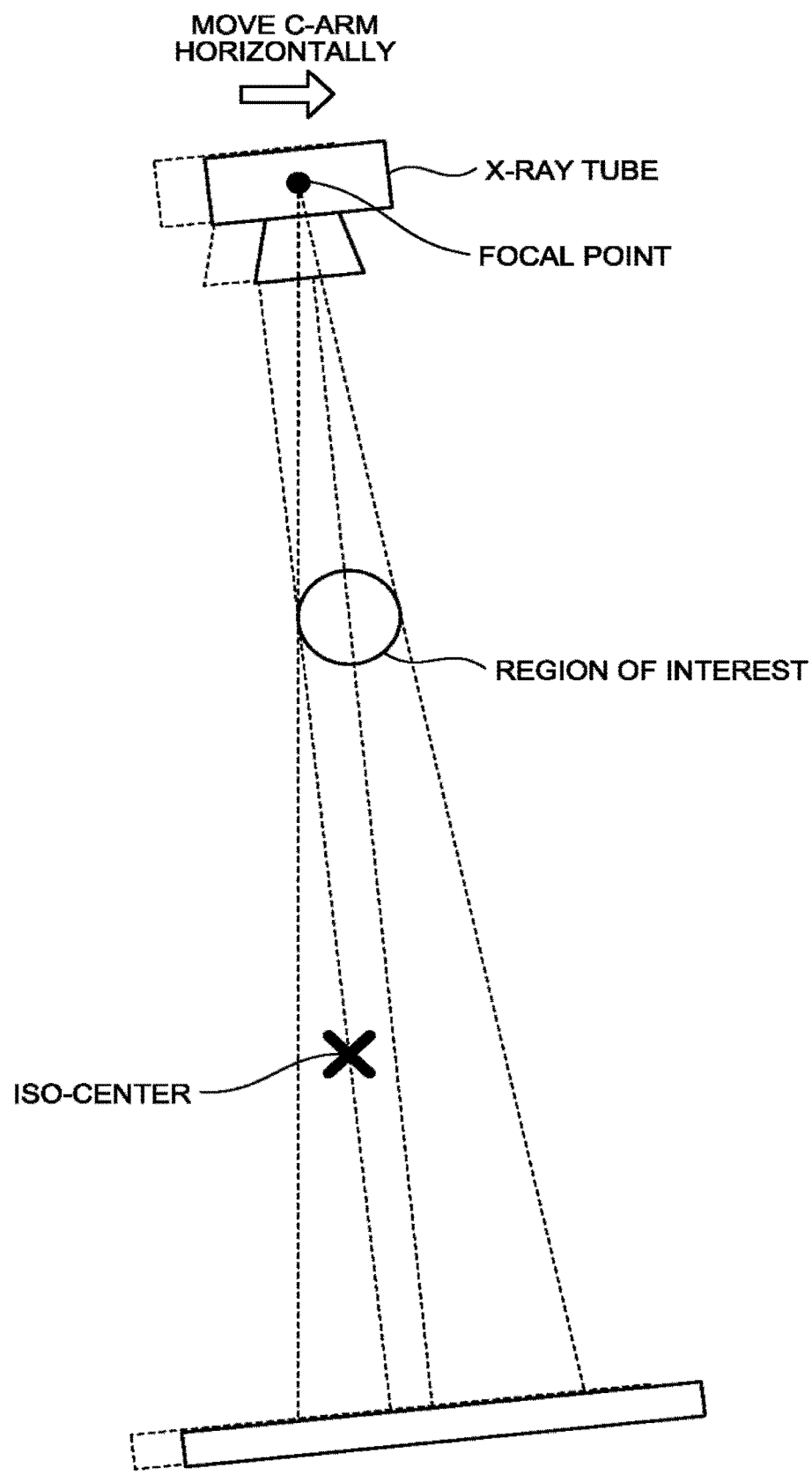
FIG. 19 is yet another drawing for explaining the process performed by the region-of-interest identifying function according to the third embodiment.

In contrast, for example, as illustrated in FIG. 19, when the shifted region-of-interest is not included in the area of the detector 12, the region-of-interest identifying function 334 moves the C-arm 13 horizontally so that the shifted region-of-interest is included in the area of the detector 12. In the example illustrated in FIG. 19, the region-of-interest identifying function 334 moves the C-arm 13 horizontally so as to arrange the center point of the region of interest to coincide with the center of the detector 12. In FIG. 19, the positions of the X-ray tube 11 and the detector 12 after the horizontal move are indicated with the solid lines, whereas the positions of the X-ray tube 11 and the detector 12 before the horizontal move are indicated with the broken lines.

As explained above, the X-ray diagnosis apparatus 1 according to the third embodiment is configured to identify the position of the region of interest with respect to the image acquisition system device and to further control the image acquisition system device so as to acquire the image of the identified position of the region of interest. With this configuration, the X-ray diagnosis apparatus 1 is able to perform the image acquisition process in such a manner that the center point of the region of interest is always at the center of the parallax images, even when the magnification ratio used by the X-ray optical system is increased.

When the magnification ratio of the X-ray optical system is increased, in some situations, the sizes of the region of interest rendered in the two pieces of parametric image data representing the parallax images may be different from each other. In those situations, it is desirable to arrange the sizes of the region of interest to be the same as each other by performing an enlarging/minifying process as an image processing process on the parametric image data. When the difference in size is so small that no impact is made on the stereoscopic viewing, it is also acceptable to use the image data in the stereoscopic display without performing any image processing process thereon.

The explanation above merely describes an example, and possible embodiments are not limited to this example. For instance, although FIG. 17 illustrates an example in which the image reading region is shifted, possible embodiments are not limited to this example. For instance, it is also acceptable to shift the detector 12 itself. More specifically, when the C-arm 13 is provided with a moving mechanism used for shifting the detector 12, it is possible to shift the detector 12 itself.

Further, for example, although FIG. 19 illustrates the example in which the center point of the region of interest is arranged to coincide with the center of the detector 12 by horizontally moving the C-arm 13, there may be situations where it is possible to arrange the centers to coincide with each other only with a horizontal move. In those situations, for example, it is acceptable to combine therewith the shifting of the image reading region explained with reference to FIG. 17. Alternatively, even when the center point of the region of interest does not coincide with the center of the detector 12, as long as the center point of the region of interest is positioned within the area of the detector 12, it is also acceptable to arrange the centers to coincide with each other by performing a parallel translation on the parametric image data as an image processing process, after the image has been acquired.

Further, in the description above, the example is explained in which the center point of the region of interest and the area of the region of interest are designated within the X-ray fluoroscopic images. However, it is also acceptable to make the designation within a three-dimensional image. For example, the operator may designate the center point of the region of interest and the area of the region of interest within a three-dimensional image by placing a three-dimensional shape pattern of the region of interest over a Multi Planar Reconstruction (MPR) cross-sectional plane of the three-dimensional image.

Other Embodiments

The present disclosure may be carried out in various different modes other than those described in the embodiments above.

The X-Ray Parametric Imaging-Purpose Image Acquisition Program

For example, by the X-ray parametric imaging-purpose image acquisition program, the image acquisition processes from the two directions are performed as a series of processes after the conditions (the image acquisition conditions and the processing conditions) are set once.

For example, the X-ray diagnosis apparatus 1 has image acquisition setting information that has configured therein, in advance, a setting where one or both of the image acquisition conditions and the processing conditions are arranged to be the same between an image acquisition process of the first difference image data and an image acquisition process of the second difference image data and between a process using the first difference image data and a process using the second difference image data. The image acquisition setting information is stored, for example, in a storage of the X-ray diagnosis apparatus 1.

Further, the processing circuitry 33 reads image acquisition setting information stored in the storage and executes the DSA image generating function 331 and the parametric image generating function 332 on the basis of the read image acquisition setting information. More specifically, the processing circuitry 33 receives, from the operator, an operation to configure image acquisition conditions and processing conditions into the image acquisition setting information. After that, the processing circuitry 33 performs a process of generating the first difference image data from the first direction and a process of generating the second difference image data from the second direction, by using the image acquisition conditions set by the operator. Further, the processing circuitry 33 performs a process of generating the first color image data and a process of generating the second color image data, by using the processing conditions set by the operator. As a result, for example, the operator is able to perform the image acquisition processes from the two directions by setting the conditions once.

An Image Processing Apparatus

Further, it is also possible to realize any of the configurations explained in the embodiments above, not only by using the X-ray diagnosis apparatus, but also by using an arbitrary image processing apparatus.

In other words, the DSA image generating function 331 generates the first difference image data by performing a subtraction on the contrast-enhanced image data and the non-contrast-enhanced image data each acquired in a time series from a first direction by using predetermined image acquisition conditions and generates the second difference image data by performing a subtraction on the contrast-enhanced image data and the non-contrast-enhanced image data each acquired in a time series from a second direction by using image acquisition conditions that are substantially the same as the predetermined image acquisition conditions. After that, the parametric image generating function 332 generates, by using predetermined processing conditions, the first color image data in which a color corresponding to a temporal change in pixel value is assigned to each of different positions in the first difference image data, and also generates, by using processing conditions that are substantially the same as the predetermined processing conditions, the second color image data in which a color corresponding to a temporal change in pixel value is assigned to each of different positions in the second difference image data. Further, the display controlling function 333 causes a stereoscopic image to be displayed on the basis of the first color image data and the second color image data.

Further, the constituent elements of the apparatuses and the devices illustrated in the drawings are based on functional concepts. Thus, it is not necessary to physically configure the constituent elements as indicated in the drawings. In other words, the specific modes of distribution and integration of the apparatuses and the devices are not limited to those illustrated in the drawings. It is acceptable to functionally or physically distribute or integrate all or a part of the apparatuses and the devices in any arbitrary units, depending on various loads and the status of use. Further, all or an arbitrary part of the processing functions performed by the apparatuses and the devices may be realized by a CPU and a computer program analyzed and executed by the CPU or may be realized as hardware using wired logic.

With regard to the processes explained in the embodiments and the modification examples above, it is acceptable to manually perform all or a part of the processes described as being performed automatically. Conversely, by using a method that is publicly known, it is also acceptable to automatically perform all or a part of the processes described as being performed manually. Further, unless noted otherwise, it is acceptable to arbitrarily modify any of the processing procedures, the controlling procedures, specific names, and various information including various types of data and parameters that are presented in the above text and the drawings.

Further, it is possible to realize the image acquisition methods (the image diagnosis aiding methods) described in the embodiments and the modification examples above, by causing a computer such as a personal computer or a workstation to execute an image acquisition computer program prepared in advance. It is possible to distribute the image acquisition methods via a network such as the Internet. Further, the image acquisition methods may be implemented as being recorded on a computer-readable recording medium such as a hard disk, a flexible disk (FD), a Compact Disk Read-Only Memory (CD-ROM), a Magneto-Optical (MO) disk, a Digital Versatile Disk (DVD), or the like and being read from the recording medium by a computer.

According to at least one aspect of the embodiments described above, it is possible to provide the image that enables the viewer to have a stereoscopic view in the parametric imaging process.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnosis apparatus comprising:
    processing circuitry configured:
    to generate first subtraction image data using contrast image data and mask image data, each of the contrast image data and the mask image data being taken in a time series by using a first image acquisition condition with X-rays radiated in a first direction;
    to generate second subtraction image data using contrast image data and mask image data, each of the contrast image data and the mask image data being taken, with X-rays radiated in a second direction, in a time series by using a second image acquisition condition that are substantially same as the first image acquisition condition;
    to generate first color image data having pixels by using a first processing condition, each pixel of the first color image data having a color according to a temporal transition at a corresponding position of the first subtraction image data;
    to generate, by using a second processing condition that is substantially same as the first processing condition, second color image data having pixels, each pixel of the second color image data having a color according to a temporal transition at a corresponding position of the second subtraction image data; and
    to cause a stereoscopic image to be displayed on a basis of the first color image data and the second color image data.

2. The X-ray diagnosis apparatus according to claim 1, wherein the processing circuitry derives an angular direction of a parallax between the first direction and the second direction in accordance with a direction in which a blood vessel extends, and
    the processing circuitry generates the first subtraction image data and the second subtraction image data for the derived first direction and for the derived second direction, respectively.

3. The X-ray diagnosis apparatus according to claim 1, wherein
    the processing circuitry generates the first color image data by identifying an inflow time of a contrast agent injected to a patient on a basis of the temporal transition in each of the different positions in the first subtraction image data and further assigning the color to each of the different positions in accordance with the identified inflow time, and
    the processing circuitry generates the second color image data by identifying an inflow time of the contrast agent injected to the patient on a basis of the temporal transition in each of the different positions in the second subtraction image data and further assigning the color to each of the different positions in accordance with the identified inflow time.

4. The X-ray diagnosis apparatus according to claim 3, wherein
    the processing circuitry generates the first subtraction image data and the second subtraction image data by arranging at least one selected from the following to be substantially same between the first image acquisition condition and the second image acquisition condition: injection condition of the contrast agent; radiation condition of the X-rays; a size of a field of view radiated by the X-rays; a distance between a focal point of an X-ray tube that radiates the X-rays and a detector for the X-rays; a position of a couch on which the patient is placed; and a rotation center of a supporting machine that supports the X-ray tube and the detector, and
    the processing circuitry generates the first color image data and the second color image data by arranging at least one selected from the following to be substantially same between the first processing condition and the second processing condition: a method for identifying the inflow time; and a color code defining the color assigned in accordance with the temporal transition.

5. The X-ray diagnosis apparatus according to claim 4, wherein the processing circuitry generates the first subtraction image data and the second subtraction image data by using the injection condition in which at least one selected from the following is substantially same between the first subtraction image data and the second subtraction image data: a time period from a time when an injection of the contrast agent is started to a time when a process of acquisition the contrast image data is started; an injection speed of the contrast agent; pressure to be applied to an injector of the contrast agent; and a rising curve before reaching the expected injection speed.

6. The X-ray diagnosis apparatus according to claim 4, wherein the processing circuitry generates the first subtraction image data and the second subtraction image data by using the radiation condition in which at least one selected from the following is substantially same between the first subtraction image data and the second subtraction image data: a frame rate of images taken by using the X-rays; an X-ray tube voltage of the X-ray tube; an X-ray tube current of the X-ray tube; a pulse width of the X-rays; a position of a collimator for the X-ray tube; a type and a thickness of a beam filter for the X-ray tube; and a position of a compensation filter for the X-ray tube.

7. The X-ray diagnosis apparatus according to claim 3, wherein the processing circuitry re-generates at least one selected from the first color image data and the second color image data, by performing a correcting process to align the inflow times calculated from a mutually-same position in the first subtraction image data and in the second subtraction image data.

8. The X-ray diagnosis apparatus according to claim 3, wherein
when using a cyclic color code defining cyclic changes of the color in response to changes in the inflow time, the processing circuitry generates the first color image data having a plurality of frames arranged in a temporal order and the second color image data having a plurality of frames arranged in a temporal order, by arranging at least one selected from the following to be substantially same between the first processing condition and the second processing condition: a quantity of the frames; and a temporal change amount between the frames used by the cyclic color code, and
the processing circuitry causes stereoscopic images to be displayed in a temporal order, on a basis of the first color image data and the second color image data representing frames that are in a mutually-same temporal phase.

9. The X-ray diagnosis apparatus according to claim 8, wherein, when having received a request to perform a non-synchronization playback process, the processing circuitry changes temporal phases of the frames displayed in the temporal order, with respect to one selected from the first color image data having the plurality of frames and the second color image data having the plurality of frames.

10. The X-ray diagnosis apparatus according to claim 1, wherein, when having received an instruction indicating that one selected from the first processing condition and the second processing condition should be changed, the processing circuitry re-generates the first color image data and the second color image data by using a processing condition after the change.

11. The X-ray diagnosis apparatus according to claim 1, wherein
the processing circuitry derives the first direction and the second direction by using at least one selected from a parallax angle that is set in advance and an angular direction of the parallax, and
the processing circuitry generates the first subtraction image data and the second subtraction image data for the derived first direction and for the derived second direction, respectively.

12. The X-ray diagnosis apparatus according to claim 1, wherein, when having received a half-pressing operation performed on an X-ray trigger button used for instructing that the X-rays be radiated, the processing circuitry changes a radiation direction of the X-rays from the first direction to the second direction.

13. The X-ray diagnosis apparatus according to claim 1, wherein, when having received a pressing operation performed on an apparatus driving button used for instructing that a radiation direction of the X-rays be changed, the processing circuitry changes the radiation direction of the X-rays from the first direction to the second direction.

14. The X-ray diagnosis apparatus according to claim 1, wherein, when having received an operation to designate a region of interest, the processing circuitry further identifies a position of the region of interest with respect to an image acquisition system device and controls the image acquisition system device so as to take an image of the identified position of the region of interest.

15. The X-ray diagnosis apparatus according to claim 1, wherein the processing circuitry generates the first subtraction image data and the second subtraction image data during a mutually-same time period, by using an X-ray tube that radiates X-rays while switching between two focal points, and
the processing circuitry generates the first color image data and the second color image data after correcting a time difference caused by the switching between the two focal points.

16. The X-ray diagnosis apparatus according to claim 1, further comprising: a storage storing image acquisition setting information that has configured therein, in advance, a setting where one or both of the image acquisition condition and the processing condition are arranged to be same between an image acquisition process of the first subtraction image data and an image acquisition process of the second subtraction image data and between a process using the first subtraction image data and a process using the second subtraction image data.

17. The X-ray diagnosis apparatus according to claim 16, wherein
the processing circuitry reads the image acquisition setting information stored in the storage and executes processes of generating the subtraction image data and the color image data on a basis of the read image acquisition setting information,
the processing circuitry receives, from an operator, an operation to set image acquisition condition and processing condition into the image acquisition setting information,
the processing circuitry performs the generating of the first subtraction image data from the first direction and the generating of the second subtraction image data from the second direction, by using the image acquisition condition set by the operator, and
the processing circuitry performs the generating of the first color image data and the generating of the second color image data, by using the processing condition set by the operator.

18. An image processing apparatus comprising:
processing circuitry configured:
to generate first subtraction image data using contrast image data and mask image data, each of the contrast image data and the mask image data being taken in a time series by using a first image acquisition condition with X-rays radiated in a first direction;
to generate second subtraction image data using contrast image data and mask image data, each of the contrast image data and the mask image data being taken, with X-rays radiated in a second direction, in a time series by using a second image acquisition condition that are substantially same as the first image acquisition condition;
to generate first color image data having pixels by using a first processing condition, each pixel of the first color image data having a color according to a temporal transition at a corresponding position of the first subtraction image data;
to generate, by using a second processing condition that is substantially same as the first processing condition, second color image data having pixels, each pixel of the second color image data having a color according to a temporal transition at a corresponding position of the second subtraction image data; and
to cause a stereoscopic image to be displayed on a basis of the first color image data and the second color image data.

19. An image diagnosis aiding method comprising:
generating first subtraction image data using contrast image data and mask image data, each of the contrast image data and the mask image data being taken in a time series by using a first image acquisition condition with X-rays radiated in a first direction;
generating second subtraction image data using contrast image data and mask image data, each of the contrast image data and the mask image data being taken, with X-rays radiated in a second direction, in a time series by using a second image acquisition condition that are substantially same as the first image acquisition condition;
generating first color image data having pixels by using a first processing condition, each pixel of the first color image data having a color according to a temporal transition at a corresponding position of the first subtraction image data;
generating, by using a second processing condition that is substantially same as the first processing condition, second color image data having pixels, each pixel of the second color image data having a color according to a temporal transition at a corresponding position of the second subtraction image data; and
causing a stereoscopic image to be displayed on a basis of the first color image data and the second color image data.

* * * * *